US012714677B2

(12) United States Patent
Virden et al.

(10) Patent No.: US 12,714,677 B2
(45) Date of Patent: Aug. 25, 2026

(54) DUAL CHAMBER SYRINGE FOR ADMINISTERING A HORMONE ENCAPSULATED BY A HYDROGEL

(71) Applicant: VITALTE LIFESCIENCES INC., Reno, NV (US)

(72) Inventors: Charles P. Virden, Reno, NV (US); Stephen Harrington, Overland Park, KS (US); Stella Vnook, Reno, NV (US)

(73) Assignee: VitalTE LifeSciences Inc., Reno, NV (US)

( * ) Notice: Subject to any disclaimer, the term of this patent is extended or adjusted under 35 U.S.C. 154(b) by 0 days.

(21) Appl. No.: 19/059,162

(22) Filed: Feb. 20, 2025

(65) Prior Publication Data

US 2025/0319020 A1 Oct. 16, 2025

Related U.S. Application Data

(60) Provisional application No. 63/556,256, filed on Feb. 21, 2024.

(51) Int. Cl.

| | |
|---|---|
| ***A61K 9/50*** | (2006.01) |
| ***A61K 9/00*** | (2006.01) |
| ***A61K 9/06*** | (2006.01) |
| ***A61K 31/565*** | (2006.01) |
| ***A61K 31/566*** | (2006.01) |
| ***A61K 31/568*** | (2006.01) |
| ***A61K 47/36*** | (2006.01) |
| ***A61M 5/19*** | (2006.01) |
| ***A61M 5/24*** | (2006.01) |

(52) U.S. Cl.

CPC .......... *A61K 9/5036* (2013.01); *A61K 9/0019* (2013.01); *A61K 9/0024* (2013.01); *A61K 9/06* (2013.01); *A61K 9/5089* (2013.01); *A61K 31/565* (2013.01); *A61K 31/566* (2013.01); *A61K 31/568* (2013.01); *A61K 47/36* (2013.01); *A61M 5/19* (2013.01); *A61M 5/2422* (2013.01); *A61M 5/2448* (2013.01); *A61M 5/2459* (2013.01)

(58) Field of Classification Search

CPC ... A61K 9/14; A61K 9/40; A61K 9/48; A61K 9/50; A61K 9/20

See application file for complete search history.

(56) References Cited

U.S. PATENT DOCUMENTS

| | | | | |
|---|---|---|---|---|
| 6,692,468 | B1 | 2/2004 | Waldenburg | |
| 2005/0281883 | A1* | 12/2005 | Daniloff | A61P 19/02 424/489 |
| 2013/0183349 | A1 | 7/2013 | Ho et al. | |
| 2015/0352056 | A1 | 12/2015 | Ramachandran et al. | |
| 2016/0303281 | A1* | 10/2016 | Salamone | A61L 27/18 |
| 2022/0175672 | A1 | 6/2022 | Grover et al. | |
| 2022/0220343 | A1 | 7/2022 | Davis et al. | |
| 2022/0233454 | A1 | 7/2022 | Ott et al. | |

FOREIGN PATENT DOCUMENTS

| | | | | |
|---|---|---|---|---|
| CN | 101953774 | A | 1/2011 | |
| CN | 113736043 | A * | 12/2021 | C08F 2/10 |
| WO | 2022256291 | A1 | 12/2022 | |
| WO | 2023044385 | A1 | 3/2023 | |

OTHER PUBLICATIONS

An et al., Drug Development and Industrial Pharmacy, vol. 29, No. 1, pp. 99-105, 2003 (Year: 2003).
International Search Report and Written Opinion for Application No. PCT/US2025/016855, dated Jul. 14, 2025, 15 pages.
Mang1r et al., Neurourology and Urodynamics. 2019; 1-8 (Year: 2019).
US Patent Office Non-Final Office Action for U.S. Appl. No. 19/059,823, dated Feb. 19, 2026, 7 pages.

* cited by examiner

*Primary Examiner* — Micah Paul Young
(74) *Attorney, Agent, or Firm* — Michael A. Kerr; Kerr IP Group, LLC

(57) ABSTRACT

A dual chamber syringes for administration of a hormone encapsulated by a hydrogel polymer is described. The dual chamber syringe includes a first chamber, a second chamber, a separator, and a plunger. The first chamber includes a crosslinked methacrylate hyaluronic acid (MHA) polymer that encapsulates the hormone. The crosslinked MHA polymer is the hydrogel polymer. The second chamber has a diluent for the crosslinked MHA polymer. The separator separates the first chamber from the second chamber. Piercing or bypassing the separator generates a mixture that includes the diluent and the crosslinked MHA polymer that encapsulates the hormone. The plunger forces the mixture through a needle.

19 Claims, 28 Drawing Sheets

DUAL CHAMBER SYRINGE FOR ADMINISTERING A HORMONE ENCAPSULATED BY A HYDROGEL

CROSS REFERENCES

This patent application claims the benefit of provisional patent application No. 63/556,256 filed on Feb. 21, 2024 entitled INJECTABLE SLOW-RELEASE FORMULATIONS. All patent applications identified above are hereby incorporated by reference.

FIELD

The present disclosure relates to apparatuses for administration of injectable slow-release hormone replenishment formulations. More particularly, the present disclosure relates to dual chamber syringes for subcutaneous injectable administration of cross-linked hydrogel polymer microbead matrices encapsulating micronized hormone therapeutics.

BACKGROUND

Hormone therapies carry significant risks of adverse effects, which can be exacerbated from inconsistent or traumatic delivery as a result of a variety of hormone therapies. Pills may be forgotten by a patient and require relatively frequent pharmacy trips to refill prescriptions. Further, oral delivery can cause gastric distress, destruction of active ingredients (medications), and/or bypass initial metabolism in the liver. Patches may be unsightly, inconvenient, uncomfortable, removed too early, and fail to accommodate individuals requiring higher levels of hormone replacement. Creams may similarly be unsightly and inconvenient, as well as delivering inadequate levels of hormones, requiring repeated application, and allowing for missed applications. Additionally, pill/oral, patch, cream, and injection therapies suffer inconsistent dosage delivery. Dosages of hormones delivered by these techniques tend to spike soon after injection, ingestion, or application, then taper quickly below efficacious medication levels. Injections of solubilized hormones require repeated and frequent trips to a doctor's office.

In contrast, implants that deliver drugs over time in a therapeutically effective dosage are useful in many fields, and especially for the controlled release of hormone therapies. The science of controlled drug release is diverse from a standpoint of both range of scientific disciplines it encompasses and the range of its applications. While extensive work has been done with subcutaneously implanted pellets, subcutaneously inserted hydrogel microparticles are a particularly efficacious mechanism of controlled drug release.

Hormone therapies that utilize subcutaneously inserted slow-release hormone therapies (e.g., hormone hydrogels or pellets) bypass the liver, do not affect clotting factors and do not increase the risk of thrombosis. Subcutaneous slow-release insertions have other practical advantages over patches, creams, and solubilized injections.

Testosterone is the major circulating androgen in males. Testosterone has been approved by the FDA and several global health authorities as a replacement therapy for men with low testosterone levels due to hypogonadism. Male hypogonadism affects 10-30% of the male population and is often under-recognized and under-treated. Different replacement formulations exist, each with specific benefits and limitations. Male hypogonadism is defined by low sex hormone levels (<12 nmol/L or <300 ng/dL), which can affect multiple organ systems, resulting in symptoms and signs of testosterone deficiency and significantly reducing quality of life.

Hypogonadism typically requires long-term treatment to manage symptoms and maintain hormonal balance. While the condition is generally not curable, it is amenable to ongoing treatment with various therapeutic options. Historically, patients have shown poor compliance to testosterone replacement therapies, displaying attrition rates of 30-90%, depending on the type of treatment and method of study. Studies have revealed concerning discontinuation rates, namely, by 6 months 34.7% of patients continued TRT, and at 12 months only 15.4% remained on the treatment.

The use of microsphere polymers to deliver drugs has a long history and spans a wide variety of active ingredients. Studies implanting testosterone in microspheres to create extended-release formulations have been performed. However, testosterone in a hydrogel formulation has not been widely prescribed due to absorption and bioavailability issues, and the stability of testosterone in a hydrogel is challenging and affects shelf life.

Thus, there is a need for hydrogel formulation with hormones that have appropriate absorption and bioavailability. Additionally, there is a need for a hydrogel formulation with hormones that is stable and provides an extended shelf life.

SUMMARY

A dual chamber syringes for administration of a hormone encapsulated by a hydrogel polymer is described. In one embodiment, the dual chamber syringe includes a first chamber, a second chamber, a separator, a plunger, and a needle. The first chamber includes a crosslinked methacrylate hyaluronic acid (MHA) polymer that encapsulates the hormone. The crosslinked MHA polymer is the hydrogel polymer. The second chamber has a diluent for the crosslinked MHA polymer. The separator separates the first chamber from the second chamber. Piercing the separator generates a mixture that includes the diluent and the crosslinked MHA polymer that encapsulates the hormone. The plunger forces the mixture through the needle.

In another embodiment, the dual chamber syringe includes a first chamber, a second chamber, a separator, a bypass, a plunger, and a needle. The first chamber includes a crosslinked methacrylate hyaluronic acid (MHA) polymer that encapsulates the hormone. The crosslinked MHA polymer is the hydrogel polymer. The second chamber has a diluent for the crosslinked MHA polymer. The separator separates the first chamber from the second chamber when the separator is in a first position. The bypass connects the first chamber to the second chamber when the separator is in a second position. Moving the separator from the first position to the second position generates a mixture that includes the diluent and the crosslinked MHA polymer that encapsulates the hormone. The plunger forces the mixture through the needle.

BRIEF DESCRIPTION OF DRAWINGS

The presently disclosed subject matter will be more fully understood by reference to the following drawings which are presented for illustrative, not limiting, purposes.

FIGS. 1A and 1B show chemical structures of Methacrylated Hyaluronic Acid (MHA) and polymeric MHA.

DESCRIPTION

Figure 2A:
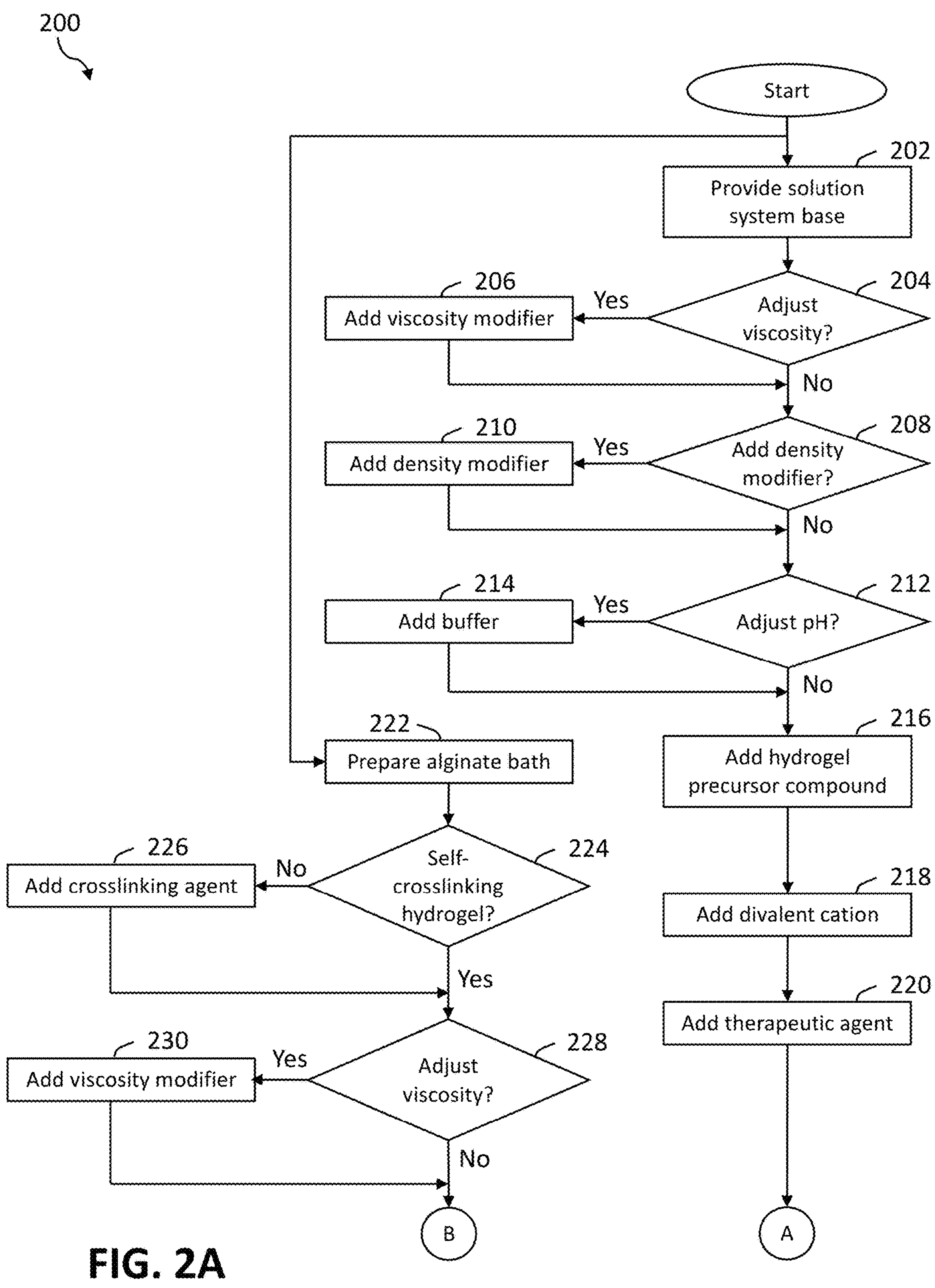
FIGS. 2A and 2B show an exemplary method of forming hydrogel containing therapeutic agents.

Persons of ordinary skill in the art will realize that the following description is illustrative and not in any way limiting. Other embodiments of the claimed subject matter will readily suggest themselves to such skilled persons having the benefit of this disclosure. It shall be appreciated by those of ordinary skill in the art that the systems and methods described herein may vary as to configuration and as to details. The following detailed description of the illustrative embodiments includes reference to the accompanying drawings, which form a part of this application. The drawings show, by way of illustration, specific embodiments in which the invention may be practiced. It is to be understood that other embodiments may be utilized and structural changes may be made without departing from the scope of the claims.

Hormone therapeutics refers to a treatment that involves the use of hormones or hormone-modulating substances to restore, regulate, or other hormone levels in the body. These therapies can be used to treat hormonal imbalances, deficiencies, or conditions related to endocrine function.

Hormone replacement therapy (HRT) can be a general term describing a method of treatment for men and women with sex hormone deficiencies, in which an exogenous hormone replenishes low or depleted hormone levels. These treatments can be required for days, week, months, or even years. HRT for women can be prescribed to treat common symptoms of e.g., menopause, including hot flashes, night sweats, and vaginal discomfort and/or dryness. HRT can also be administered to treat a cardiovascular disease or condition, including protecting the heart and individual cardiac myocytes from injuries related to ischemia. After a heart attack or long periods of hypertension, HRT can inhibit the adverse effects of pathologic remodeling of the heart.

As discussed above in the Background, HRT treatment can be delivered through a variety of routes, for example, a transdermal patch, a transdermal gel, a slow-release vaginal ring, cream or spray, and/or daily oral pills, but each of these routes has one or more compliance issues. Provided herein are slow-release compositions that comprise a hormone (e.g., estradiol or bioidentical estradiol) for administration of the hormone which can have the advantage of increasing compliance and quality of life for the patient or subject. As disclosed herein, a patient or subject can be a mammal, a human, a man, or a woman, which can be in need of the hormone.

Deposits of subcutaneous brown adipose tissue (BAT) have superior blood supplies which beneficially improve medication uptake from subcutaneously inserted hydrogels. Such subcutaneous BAT is known to exist in the anterior abdominal wall and along the vertebral column. As such, the love-handle region, beside the vertebral column (spine), and anterior sides of the abdomen (below and beside the belly/tummy fat) are possible hydrogel delivery locations. These locations are preferred for men due to the typically larger doses of medication required as compared to women, and the corresponding larger hydrogel volumes that must be inserted in order to deliver larger doses of medication. Other possible delivery locations are selected for patient comfort, such as the tensor fascia on the thigh, and the subcutaneous tissue surrounding the gluteus medius or maximus.

Micronized testosterone USP is commonly used in various pharmaceutical formulations, such as capsules or tablets, intended for oral administration. It can also be used in topical formulations like gels or creams. Micronized testosterone is often prescribed for hormone replacement therapy (HRT) in men with low testosterone levels (hypogonadism) and may also have applications in certain conditions affecting hormone levels in women. Additionally, micronized estradiol may also be prescribed for women.

Micronized testosterone (or estrogen/estradiol) has been finely ground into smaller particles to improve absorption. Micronized testosterone is commonly used in non-injectable forms such as gels, creams, or oral formulations. In the embodiments presented herein, which is typically used in non-injectable forms, is converted to an injectable product when encapsulated by the MHA hydrogel polymer described herein.

After administering the hydrogel having the illustrative micronized testosterone into the subcutaneous tissue, the testosterone is released slowly and binds to androgen receptors. Proper dosing is critical because excess testosterone is primarily metabolized into dihydrotestosterone (DHT), estrogen, along with other various metabolites that are excreted through the liver and kidney.

In the illustrative embodiments, the microbeads are sterile hydrated hydrogel spherical particles that include cross-linked hyaluronic acid in a buffered storage solution. The microbeads are formed from polymers, such as hyaluronic acid, polyethylene glycol, polyvinyl glycol and gelatin. These polymers, when mixed, are made to polymerize with bioactive compounds to produce encapsulated therapeutics.

More generally, the microbeads can be used for a variety of applications such as encapsulating an API for the controlled release of small molecules and biologics. In the context of delivery of cells, the microspheres provide two important advantages, namely, the ability to keep adherent cell types viable during transportation and administration by acting as a scaffold for necessary attachment sites, and by absorbing and dissipating shear forces applied to cells that can disrupt the cell membrane and lead to premature cell death.

In one therapeutic embodiment, an inserted hydrogel releases medication consistently for 2 months before requiring reinsertion of additional hydrogel medication. Upon reaching termination of this 2-month period, the location of the second administration of hydrogel medication may be rotated. For example, the first administration of hydrogel medication may be placed above a patient's beltline in their right love-handle region, while the second administration of hydrogel medication may be placed above the patient's beltline in their left love-handle region. This side-to-side rotation every 2 months allows for complete healing of the first administration site in the patient's right love-handle region prior to any third or re-administration to the patient's right love-handle region, and similarly for re-administration to the patient's left love-handle region.

In the illustrative embodiments presented herein, the testosterone hydrogel formulation provides a controlled release of testosterone levels for approximately one (1) month. In a more short-term testosterone hydrogel formulation, the controlled release of testosterone ranges from one (1) week to one (1) month. With respect to a long-term testosterone hydrogel formulation, the controlled release of testosterone ranges from one (1) month to six (6) months. The dosage of the testosterone hydrogel formulation may also be dependent on individuals' baseline testosterone level, body mass index (BMI), and body composition such the percentage of body fat and lean muscle mass.

In general, hydrogel implantation requires fewer visits to a doctor's office during a course of treatment compared to solubilized medication injections (lasting for only a matter of days), provides more consistent dosages than patches, creams, and pills, and requires a much less invasive insertion site than medication pellet implantation. This makes hydrogel injections more efficacious than patches, creams, pills, and less painful than implants or pellets, and more cost effective than solubilized medication injections requiring frequent trips to a doctor's office.

As described in further detail below, the illustrative micronized testosterone is bound to the hydrogel. By way of example and not of limitation, the illustrative hydrogel described herein includes a crosslinked methacrylated hyaluronic acid (MHA) polymer. In the illustrative embodiment, the testosterone hydrogel is administered with a dual chamber syringe, in which the first chamber includes the testosterone hydrogel and the second chamber includes a hydrogel solvent. Illustrative hydrogel solvents include water, a buffered aqueous solution, a saline solution, glycerol, polyethylene glycol, propylene glycol, dimethyl sulfoxide (DMSO), diluted ethanol, biocompatible ionic liquids, water-alcohol mixtures, and other such solvents. More generally, the solvents must be biocompatible, sterile, support gelation conditions, and satisfy application specific requirements.

In one embodiment, the illustrative hydrogel is a biodegradable hydrogel formulation intended to be administered via a subcutaneous (SC) injection for the treatment of hypogonadism in adult males. In this illustrative embodiment, the hydrogel is a Methacrylate Hyaluronic Acid (MHA) polymer excipient that includes a crosslinked MHA polymer for extended-release of testosterone. The MHA polymer is a microbead polymer that encapsulates testosterone and provides for the slow release of testosterone.

The hydrogel compositions and insertion methods disclosed herein can be used for various regimens that include hormone therapy, pain management, and addiction treatment. Further, the hydrogel compositions and insertion methods disclosed herein can be employed in veterinary treatments as well.

Chronic pain management techniques include subdermal surgical insertion of a reservoir and/or pump connected to a catheter that runs directly to the patient's spine to deliver morphine or other anesthetics. This technique may afford relief to a patient for several months between doctor's visits, however the system costs tens of thousands of dollars. In contrast, the hydrogel compositions disclosed herein are much more affordable, allowing for single-use disposable embodiments that deliver relief for several months.

Disclosed herein are compositions, pharmaceutical compositions, methods of treating disease or conditions with these in a subject, kits containing the compositions and pharmaceutical compositions, and methods of making the compositions, pharmaceutical compositions, and kits.

Definitions

Throughout this application, various aspects may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

The terms "microsphere" and "microparticle" are used herein interchangeably generally to refer to spheres, spherical objects, semi-spherical objects, or droplets having a diameter or surface-to-surface dimension of <2000 μm. In particular, the terms "microsphere," "microbead," and "microparticle" are used herein interchangeably to refer to spherical, semi-spherical, or droplets of hydrogel or of core shell hydrogel particles.

The term "microbead" is used herein as a specific example of "microsphere" and "microparticle." More particularly, the term "microbead" is used to refer to the final hydrogel particle products encapsulating a therapeutic agent after removal of any outer layer.

The term "biocompatible" can mean not harmful to living tissue, and/or not biologically or otherwise undesirable, in that something that can be biocompatible can be administered to a subject without excessive toxicity, irritation, allergic, and/or immunogenic response, and/or does not cause any undesirable biological effects.

As used herein, the term 'about' a number can refer to that number plus or minus 10% or plus or minus 5% of that number. The term 'about' a range can refer to that range minus 10% of its lowest value and plus 10% of its greatest value. The term 'about' a range can refer to that range minus 5% of its lowest value and plus 5% of its greatest value.

As used in the specification and claims, the singular forms "a", "an" and "the" include plural references unless the context clearly dictates otherwise. For example, the term "a sample" includes a plurality of samples, including mixtures thereof.

Unless otherwise indicated, open terms for example "contain," "containing," "include," "including," and the like mean comprising.

In some instances herein, the terms "slow-release," "extended release," and "controlled release" can be used interchangeably.

The terms "determining", "measuring", "evaluating", "assessing," "assaying," and "analyzing" are often used interchangeably herein to refer to forms of measurement and include determining if an element may be present or not (for example, detection). These terms may include quantitative and/or qualitative determinations. Assessing may be alternatively relative or absolute. "Detecting the presence of" includes determining the amount of something present, as well as determining whether it may be present or absent.

The term "at least partially" may refer to a qualitative condition that exhibits a partial range or degree of a feature or characteristic of interest. For example, at least partially can comprise a partial range or degree of a feature or characteristic of interest that is at least about: 5%, 10%, 20%, 30%, 40%, 50%, 60%, 70%, 75%, 80%, 85%, 90%, 95%, 99%, or 100% of the feature or characteristic.

The term "substantially" or "essentially" can refer to a qualitative condition that exhibits an entire or nearly total range or degree of a feature or characteristic of interest. In some cases, substantially can refer to a total range or degree of a feature or characteristic of interest by about plus or minus: 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. In some cases, substantially can refer to at least about: 70%, 75%, 80%, 85%, 90%, 95%, 99%, or 100% of the total range or degree of a feature or characteristic of interest.

The term "substantially free," as used herein means that the ingredient is not intentionally added to the composition, although incidental impurities may occur. For example, the hydrogel precursor solution compositions may comprise less than about 0.05% by weight, less than about 0.01% by weight, or 0% by weight of an impurity ingredient, based upon the total weight of the hydrogel precursor solution emulsion taken as 100% by weight.

The section headings used herein are for organizational purposes only and are not to be construed as limiting the subject matter described.

The terms "dilutant" and "diluent" are used interchangeably herein, and generally refer to a substance that reduces the concentration of a mixture or solution.

The terms "subject," "individual," or "patient" are often used interchangeably herein. A "subject" may be a biological entity. The biological entity may be a plant, animal, or a microorganism, including, for example, a eukaryotic cell, a bacteria, a virus, a fungi, and a protozoa. The subject may be tissues, cells and their progeny of a biological entity obtained in vivo or cultured in vitro. The subject may be a mammal. The mammal may be a human. The subject may be diagnosed or suspected of being at high risk for a disease. In some cases, the subject may not be necessarily diagnosed or suspected of being at high risk for the disease. In some cases, the subject may be healthy (e.g., the subject may not have a significant disease). In some cases, a subject can be a child or an adult. In some cases, a subject can be about 1 day of age to about 18 years of age, 1 day of age to about 120 years of age, 18 years of age to about 120 years of age, 40 years to age to about 80 years of age, or 60 years of age to about 120 years of age. As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit may be achieved with the eradication or amelioration of one or more of the physiological symptoms associated with the underlying disorder such that an improvement may be observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For a prophylactic benefit, a subject at risk of developing a particular disease, or to a subject reporting one or more of the physiological symptoms of a disease may undergo treatment, even though a diagnosis of this disease may not have been made.

The term "surface-to-surface" refers generally to the measurement of the linear distance between two points on the droplet's surface opposite one another. For the case of a spherical droplet, this measurement is defined as the diameter of the sphere. For a flattened or deformed droplet, this measurement is defined as the widest point of the droplet, i.e., the major axis of the droplet.

The term "micronized" refers generally to the process of reducing a bulk compound in particle size to solid particles in the micrometer or nanometer scale. Micronized testosterone USP refers to a specific formulation of testosterone that has been micronized and meets the quality standards set by the United States Pharmacopeia (USP). Micronizing testosterone enhances its solubility and absorption. Since smaller particles have a larger surface area, this results in improved bioavailability. The designation "USP" indicates that the testosterone product meets the stringent quality, purity, and potency standards established by the United States Pharmacopeia, which ensures that the product is safe for use and effective for its intended purpose.

Generally, an "excipient" is an inactive substance used in drug formulation to serve as a vehicle or medium for the active pharmaceutical ingredient (API). Excipients do not have medicinal effects themselves but play essential roles in ensuring the stability, delivery, and usability of the medication.

A "therapeutically effective amount" refers to an amount of a composition as disclosed herein with or without additional agents that is effective to achieve its intended purpose, for example to treat a disease. Individual patient needs may vary. Generally, the dosage required to provide an effective amount of the composition will vary, depending on the age, health, physical condition, sex, weight, extent of the disease of the recipient, frequency of treatment and the nature and scope of the disease or condition.

As used herein, a "dose" can refer to a measured quantity of a therapeutic agent to be taken at one time.

As used herein, the term "unit dose" or "dosage form" may be used interchangeably and may be meant to refer to pharmaceutical drug products in the form in which they are marketed for use, with a specific mixture of active ingredients and inactive components or excipients, in a particular configuration, and apportioned into a particular dose to be delivered. The term "unit dose" may also sometimes encompass non-reusable packaging. More than one unit dose may refer to distinct pharmaceutical drug products packaged together, or to a single pharmaceutical drug product containing multiple drugs and/or doses. Types of unit doses may vary with the route of administration for drug delivery, and the substance(s) being delivered. A solid unit dose may be the solid form of a dose of a chemical compound used as a pharmaceutically acceptable drug or medication intended for administration or consumption.

As used herein, the terms "therapeutic agent," "medication," "medicinal," and "active pharmaceutical ingredient (API)" are synonymous and used interchangeably. These terms include, but are not limited to, hormones, hormone therapy, pain medication, addiction therapy, and other such drugs. More specifically, these terms may be used to refer to drugs such as testosterone, estradiol (estrogen), fentanyl, morphine, various opiates, naltrexone, lidocaine and other such drugs. By way of example and not of limitation, "therapeutic agent" may refer to hormones, opioids, numbing agents, and competitive antagonists in metabolic pathways. For another example, "medication" may refer to therapeutic agents that blocks receptors in the brain, which aid in the treatment of addictive disorders including, but not limited to, alcohol and narcotics.

As used herein, the term "hormones" may also refer to synthetic hormones, bioidentical hormones and natural hormones. Synthetic hormones frequently do not have the same structure as endogenous hormones. Synthetic hormones may mimic the effects of endogenous hormones on many biological pathways, but they rarely offer the same effectiveness across all biological pathways. Bioidenticals are exact structural replicas of endogenous hormones and are reported to have much lower incidences of side effects as compared to synthetic hormones. Bioidentical hormones may be derived from plants, such as soy or wild yams. Bioidentical hormones are sometimes defined as molecules identical to a hormone produced by the human body. Natural hormones are those produced in nature by various organisms, and similar to bioidenticals, are identical to a hormone produced by the human body. As used herein, the hormones can include an: adrenaline, melatonin, noradrenaline, testosterone, estrogen, estradiol, triiodothyronine, thyroxine, dopamine, prostaglandin, leukotriene, prostacyclin, or thromboxane. In some cases, as used herein hormones can include an: epinephrine, melatonin, noradrenaline, norepinephrine, triiodothyronine, thyroxine, dopamine, prostaglandins, leukotrienes, prostacyclin, thromboxane, amylin, anti-müllerian hormone, adiponectin, adrenocorticotropic hormone, corticotropin, angiotensinogen, angiotensin, antidiuretic hormone, vasopressin, arginine vasopressin, atrial natriuretic peptide, atriopeptin, brain natriuretic peptide, calcitonin, cholecystokinin, corticotropin-releasing hormone, cortistatin, enkephalin, endothelin, erythropoietin, follicle-stimulating hormone, galanin, gastric inhibitory polypeptide, gastrin, ghrelin, glucagon, glucagon-like peptide-1, gonadotropin-releasing hormone, growth hormone-releasing hormone, hepcidin, human chorionic gonadotropin, human placental lactogen, growth hormone, inhibin, insulin, hypoglycemic hormone, insulin-like growth factor, somatomedin, leptin, lipotropin, luteinizing hormone, melanocyte stimulating hormone, motilin, orexin, osteocalcin, oxytocin, pitocin, pancreatic polypeptide, parathyroid hormone, pituitary adenylate cyclase-activating peptide, prolactin, leuteotropic hormone, prolactin-releasing hormone, relaxin, renin, secretin, somatostatin, growth hormone-inhibiting hormone, growth hormone release-inhibiting hormone, somatotropin release-inhibiting factor, somatotropin release-inhibiting hormone, thrombopoietin, thyroid-stimulating hormone, thyrotropin, thyrotropin-releasing hormone, vasoactive intestinal peptide, guanylin, uroguanylin, a synthetic version of any these hormones, a bioidentical version of any of these hormones, or any combination thereof.

In some cases, a composition herein can comprise a steroid such as a testosterone, a dehydroepiandrosterone, an androstenedione, a dihydrotestosterone, an aldosterone, an estradiol, an estrone, an estriol, a cortisol, a progesterone, a calcitriol, a calcidiol, a synthetic version of any these hormones, a bioidentical version of any of these hormones, or any combination thereof. As used herein, reference to a therapy, a compound, or a composition, includes reference to any salt, solvate, ester, or polymorph of the therapy, the compound, or the composition.

A "salt" can include a pharmaceutically acceptable salt. In some embodiments, the pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; inorganic acid salts such as hydrochloride, hydrobromide, phosphate, sulphate and the like; organic acid salts such as citrate, lactate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate and the like. In some instances, a salt of a polypeptide or derivative thereof or a compound can be a Zwitterionic salt.

In some embodiments, a pharmaceutical composition comprising the salt of the pharmaceutically active ingredient can comprise an organic salt or an inorganic salt. In some cases, an organic salt may comprise a phosphinate (e.g., sodium hypophosphite), a hydrazinium salt, a urate, a diazonium salt, an oxalate salt, a tartrate, a choline chloride. An example of an inorganic salt may be sodium chloride, calcium chloride, magnesium chloride, sodium bicarbonate, potassium chloride, sodium sulfate, calcium carbonate, calcium phosphate, or any combination thereof. In some cases, a salt comprises an HCl salt, an ascorbic acid salt, a mandelic acid salt, an aspartic acid salt, a carbonic acid salt, a citric acid salt, a formic acid salt, a glutamic acid salt, a lactic acid salt, a lauric acid salt, a maleic acid salt, a borate salt, a bitartrate salt, a palmitic acid salt, a phosphoric acid salt, or any combination thereof.

In some embodiments, a pharmaceutical composition can comprise an excipient, a carrier, and/or a diluent. In some embodiments, an excipient, a carrier, and/or a diluent can be a pharmaceutically acceptable excipient, carrier, and/or diluent. In some embodiments, a composition herein can comprise one or more of the following excipients: acacia, acesulfame potassium, acetic acid-glacial, acetone, acetyltributyl citrate, acetyltriethyl citrate, adipic acid, agar, albumin, alcohol, alginic acid, aliphatic polyesters, alitame, almond oil, alpha tocopherol, aluminum hydroxide adjuvant, aluminum monostearate, aluminum oxide, aluminum phosphate adjuvant, ammonia solution, ammonium alginate, ammonium chloride, ascorbic acid, ascorbyl palmitate, aspartame, attapulgite, bentonite, benzalkonium chloride, benzethonium chloride, benzoic acid, benzyl alcohol, benzyl benzoate, boric acid, bronopol, butylated hydroxyanisole, butylated hydroxytoluene, butylene glycol, butylparaben, calcium acetate, calcium alginate, calcium carbonate, calcium chloride, calcium hydroxide, calcium lactate, calcium phosphate-dibasic anhydrous, calcium phosphate-dibasic dihydrate, calcium phosphate-tribasic, calcium silicate, calcium stearate, calcium sulfate, canola oil, carbomer, carbon dioxide, carboxymethylcellulose calcium, carboxymethylcellulose sodium, carrageenan, castor oil, castor oil-hydrogenated, cellulose-microcrystalline, cellulose-microcrystalline and carboxymethylcellulose sodium, cellulose-powdered, cellulose-silicified microcrystalline, cellulose acetate, cellulose acetate phthalate, *ceratonia*, ceresin, cetostearyl alcohol, cetrimide, cetyl alcohol, cetylpyridinium chloride, chitosan, chlorhexidine, chlorobutanol, chlorocresol, chlorodifluoroethane (hcfc), chlorofluorocarbons (cfc), chloroxylenol, cholesterol, citric acid monohydrate, coconut oil, colloidal silicon dioxide, coloring agents, copovidone, corn oil, corn starch and pregelatinized starch, cottonseed oil, cresol, croscarmellose sodium, crospovidone, cyclodextrins, cyclomethicone, denatonium benzoate, dextrates, dextrin, dextrose, dibutyl phthalate, dibutyl sebacate, diethanolamine, diethyl phthalate, difluoroethane (hfc), dimethicone, dimethyl ether, dimethyl phthalate, dimethyl sulfoxide, dimethylacetamide, disodium edetate, docusate sodium, edetic acid, erythorbic acid, erythritol, ethyl acetate, ethyl lactate, ethyl maltol, ethyl oleate, ethyl vanillin, ethylcellulose, ethylene glycol stearates, ethylene vinyl acetate, ethylparaben, fructose, fumaric acid, gelatin, glucose-liquid, glycerin, glyceryl behenate, glyceryl monooleate, glyceryl monostearate, glyceryl palmitostearate, glycine, glycofurol, guar gum, hectorite, heptafluoropropane (hfc), hexetidine, hydrocarbons (hc), hydrochloric acid, hydrophobic colloidal silica, hydroxyethyl cellulose, hydroxyethylmethyl cellulose, hydroxypropyl betadex, hydroxypropyl cellulose, hydroxypropyl cellulose-low-substituted, hydroxypropyl starch, hypromellose, hypromellose acetate succinate, hypromellose phthalate, imidurea, inulin, iron oxides, isomalt, isopropyl alcohol, isopropyl myristate, isopropyl palmitate, kaolin, lactic acid, lactitol, lactose-anhydrous, lactose-inhalation, lactose-monohydrate, lactose-monohydrate and corn starch, lactose-monohydrate and microcrystalline cellulose, lactose-monohydrate and povidone, lactose-monohydrate and powdered cellulose, lactose-spray-dried, lanolin, lanolin-hydrous, lanolin alcohols, lauric acid, lecithin, leucine, linoleic acid, macrogol 15 hydroxystearate, magnesium aluminum silicate, magnesium carbonate, magnesium oxide, magnesium silicate, magnesium stearate, magnesium trisilicate, maleic acid, malic acid, maltitol, maltitol solution, maltodextrin, maltol, maltose, mannitol, medium-chain triglycerides, meglumine, menthol, methionine, methylcellulose, methylparaben, mineral oil, mineral oil-light, mineral oil and lanolin alcohols, monoethanolamine, monosodium glutamate, monothioglycerol, myristic acid, myristyl alcohol, neohesperidin dihydrochalcone, neotame, nitrogen, nitrous oxide, octyldodecanol, oleic acid, oleyl alcohol, olive oil, palmitic acid, paraffin, peanut oil, pectin, pentetic acid, petrolatum, petrolatum and lanolin alcohols, phenol, phenoxyethanol, phenylethyl alcohol, phenylmercuric acetate, phenylmercuric borate, phenylmercuric nitrate, phospholipids, phosphoric acid, polacrilin potassium, poloxamer, polycarbophil, polydextrose, poly (dl-lactic acid), polyethylene glycol, polyethylene oxide, polymethacrylates, poly(methyl vinylether/maleic anhydride), polyoxyethylene alkyl ethers, polyoxyethylene castor oil derivatives, polyoxyethylene sorbitan fatty acid esters, polyoxyethylene stearates, polyoxylglycerides, polyvinyl acetate phthalate, polyvinyl alcohol, potassium alginate, potassium alum, potassium benzoate, potassium bicarbonate, potassium chloride, potassium citrate, potassium hydroxide, potassium metabisulfite, potassium sorbate, povidone, propionic acid, propyl gallate, propylene carbonate, propylene glycol, propylene glycol alginate, propylparaben, propylparaben sodium, pyrrolidone, raffinose, saccharin, saccharin sodium, safflower oil, saponite, sesame oil, shellac, simethicone, sodium acetate, sodium alginate, sodium ascorbate, sodium benzoate, sodium bicarbonate, sodium borate, sodium carbonate, sodium chloride, sodium citrate dihydrate, sodium cyclamate, sodium formaldehyde sulfoxylate, sodium hyaluronate, sodium hydroxide, sodium lactate, sodium lauryl sulfate, sodium metabisulfite, sodium phosphate-dibasic, sodium phosphate-monobasic, sodium propionate, sodium starch glycolate, sodium stearyl fumarate, sodium sulfite, sodium thiosulfate, sorbic acid, sorbitan esters (sorbitan fatty acid esters), sorbitol, soybean oil, starch, starch-pregelatinized, starch-sterilizable maize, stearic acid, stearyl alcohol, sucralose, sucrose, sucrose octaacetate, sugar-compressible, sugar-confectioner's, sugar spheres, sulfobutylether b-cyclodextrin, sulfur dioxide, sulfuric acid, sunflower oil, suppository bases-hard fat, tagatose, talc, tartaric acid, tetrafluoroethane (hfc), thaumatin, thimerosal, thymol, titanium dioxide, tragacanth, trehalose, triacetin, tributyl citrate, tricaprylin, triethanolamine, triethyl citrate, triolein, vanillin, vegetable oil-hydrogenated, vitamin e polyethylene glycol succinate, water, wax-anionic emulsifying, wax-carnauba, wax-cetyl esters, wax-microcrystalline, wax-nonionic emulsifying, wax-white, wax-yellow, xanthan gum, xylitol, zein, zinc acetate, or zinc stearate.

Although the terms "hyaluronan" and "hyaluronic acid" are used interchangeably, there is a distinction between these terms. Hyaluronic acid refers to the acidic form that includes a carboxylic acid group. Hyaluronan is a broader term that includes all forms of the molecule such as neutral and salt forms and emphasizes the molecule as a polymer rather than the acidic form.

In some cases, a composition herein can comprise a carrier and/or a dilutant. In some cases, a carrier or a dilutant can be a pharmaceutically acceptable carrier and/or dilutant. In some instances, a carrier or dilutant can comprise a water, an alcohol, a salt solution (e.g., saline), or a mixture thereof. In some instances, a carrier can comprise a carbohydrate (e.g., a sugar), a buffer, a salt, a pH adjuster, or any combination thereof. In some cases, sodium phosphate, citric acid, acetic acid, tromethamine, histidine, gluconic, lactic acid, tartaric acid, aspartic acid, glutamic acid, a citric acid cycle intermediate, or any combination thereof can be a buffer. In some cases, citrate can be used as a buffer. In some cases, a carrier can be a substrate used in the process of drug delivery. In some cases, a carrier can contribute a product's attributes such as stability, biopharmaceutical profile, and/or appearance. In some cases, a carrier can be an organic excipient.

Generation of Microspheres Containing Therapeutic Agent

The hydrogel excipient microparticles encapsulating an API disclosed herein are generally formed by extruding droplets of a hydrogel precursor solution through an orifice, so that the droplets contact an alginate solution bath. Upon entry into the alginate solution, the hydrogel precursor droplet is encapsulated by an alginate shell and itself begins a slower process of gelation. The core/shell particles can then be collected by straining or filtering the alginate solution. The core/shell particles are then washed with a buffer that de-crosslinks the alginate comprising the particle shell, leaving the hydrogel core particle (now crosslinked to form a gel) intact and available for collection or further manipulation.

In an illustrative embodiment provided herein, the API is testosterone. Additionally, the API may also be estradiol, estrogen, or other such steroid hormone derived from cholesterol. The excipient in the illustrative embodiments described herein is a "hydrogel excipient." The hydrogel excipient described herein is manufactured using Likarda's patented Core-Shell Spherification (CSS)® technology, which is described further in inter alia U.S. Patent Publication, 2022/0233454, U.S. Patent Publication 2024/0091413, and PCT Publication 2015/187862. The Core-Shell Spherification technology utilizes a non-interfering, biocompatible, non-emulsion-based method of producing hydrogel microspheres from polymers with slow gelation rates.

In some embodiments, the hydrogel excipient is a suspension of microspheres composed of a three-dimensional network of covalently crosslinked hyaluronan methacrylate polymers and an aqueous solvent. In the illustrative embodiment presented herein, the illustrative hydrogel excipient includes crosslinked hyaluronan methacrylate hydrogel microspheres. In a non-limiting embodiment, the illustrative hydrogel excipient is generated with free radical photopolymerization of soluble hyaluronan methacrylate pre-polymers.

The hydrogel excipient encapsulates one or more APIs. In general, the active ingredients that are loaded into the hydrogel excipient may include cells, antibodies, small molecules, large molecules, peptides, and other such compounds. The hydrogel excipient that encapsulates the illustrative testosterone API is then injected into the subcutaneous tissue. The API that is encapsulated by the hydrogel excipient is then slowly released into the subcutaneous tissue.

In this context, encapsulation of the APIs refers to the inclusion of APIs on, within, and/or throughout the hydrogel matrix formed by crosslinking hydrogel precursor polymers. Thus, encapsulated APIs may be within a hydrogel microbead, within the matrix of a hydrogel, dissolved in a precursor solution solvent system, and/or adhered to one or more surface of the hydrogel matrix (whether that hydrogel matrix comprises a hydrogel microbead or a hydrogel cream).

Figures 1A, 1B:
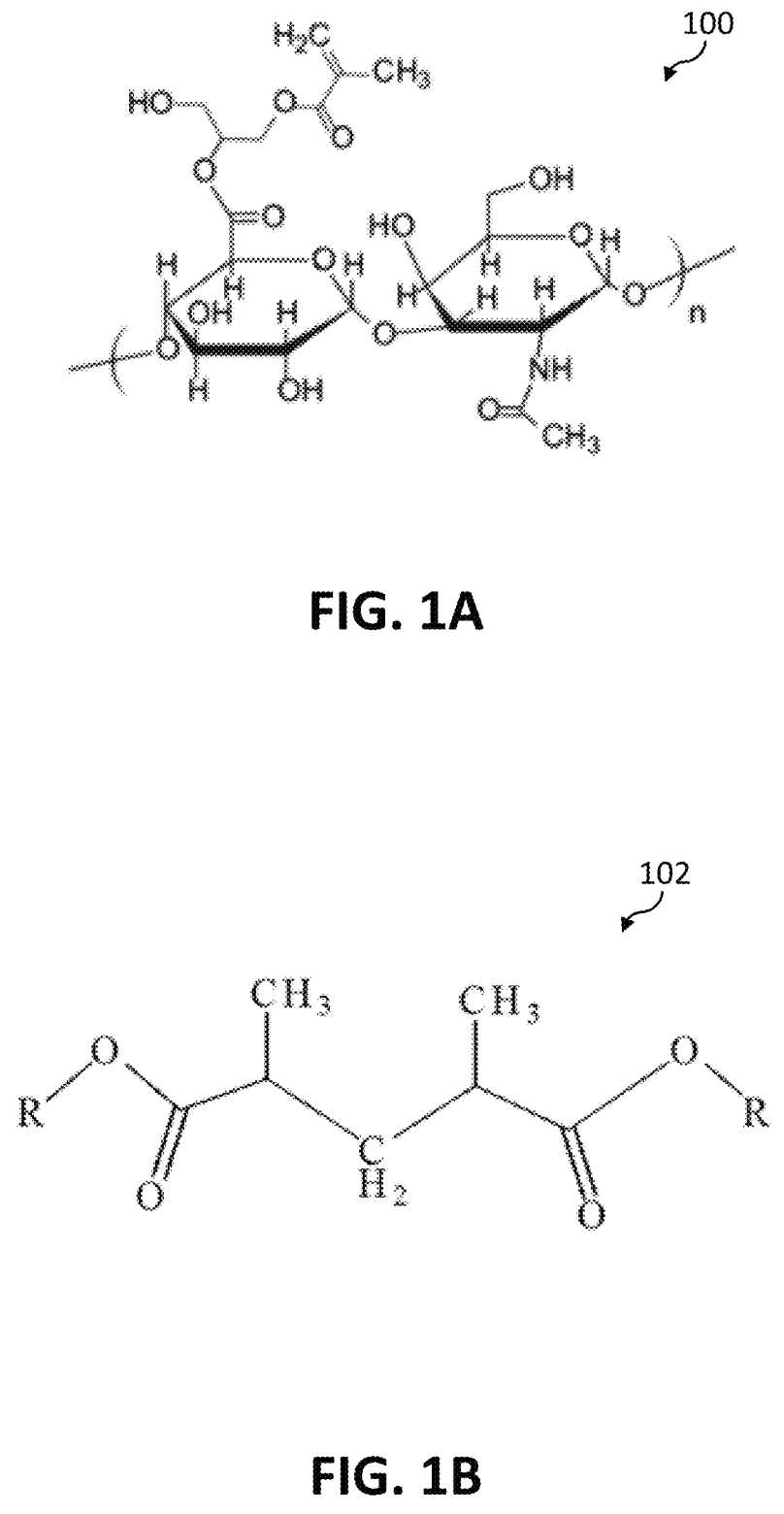

The molecular structure of uncrosslinked hyaluronan methacrylate 100 (starting material) is presented in FIG. 1A, while the structure of crosslinked hyaluronan methacrylate 102 is shown in FIG. 1B. In FIG. 1B, "R" is hyaluronan. The crosslinked hyaluronan methacrylate excipient is intended to be used as a carrier that can encapsulate various active ingredients with the intention of delivering them safely into the body. Various active ingredients can be loaded into the hydrogel including cells, antibodies, small molecules, and peptides. After the inclusion of such active ingredients, a population of therapeutic agent-laden hydrogel microspheres can be injected locally into the body, and the encapsulated therapeutic slowly released over time as a function of both material degradation and passive diffusion of the therapeutic agent.

One manufacturing process for the hydrogel excipient involves three steps. The first step includes the generation of the core shell constructs. The first step includes preparing a hydrogel precursor solution with calcium chloride, which is then extruded into an alginate bath using a droplet generation system. The calcium ions diffuse into the alginate and generate a spherical core-shell of crosslinked alginate shells that surround uncrosslinked precursor cores.

In the second step of the hydrogel excipient manufacturing process, the precursor core is crosslinked by activation of a photoinitiator with ultraviolet radiation. In the third step, the alginate shell is removed by chelation with citrate ions, which yields only the crosslinked hydrogel microsphere. The microsphere is then rinsed of residual process media and formulated in a specific resuspension.

Any suitable apparatus can be used, and such apparatus will generally comprise a chamber for holding the hydrogel precursor solution, with the chamber being in fluid communication with a fluid passage that terminates in a dispensing outlet or tip. The dispensing tip will have an orifice through which the hydrogel precursor solution is expelled as a droplet. The technique can be executed using a simple apparatus, such as a syringe and needle, as well as machines specifically designed for droplet generation, such as the Likarda® Core Shell Spherification® (CSS) instrument manufactured by Likarda from Kansas City, Missouri. The desired size of the droplet can be controlled based upon the cross-sectional dimension of the orifice, the viscosity of the hydrogel precursor solution, and relative viscosity of the alginate solution.

In some embodiments, the microbeads described herein have a diameter of approximately 0.07 mm and include a Methacrylate Hyaluronic Acid (MHA) polymer carrier, which stabilizes the micronized testosterone.

In some embodiments, the chemical composition described herein utilizes a different crosslinking agent than the crosslinking agents that have been previously used in FDA approved products. More specifically, the crosslinking agent used in the illustrative embodiment is a methacrylate that is subject to free radical photopolymerization via Lithium phenyl-2,4,6-trimethylbenzoylphosphinate (LAP) initiator.

Figure 2B:
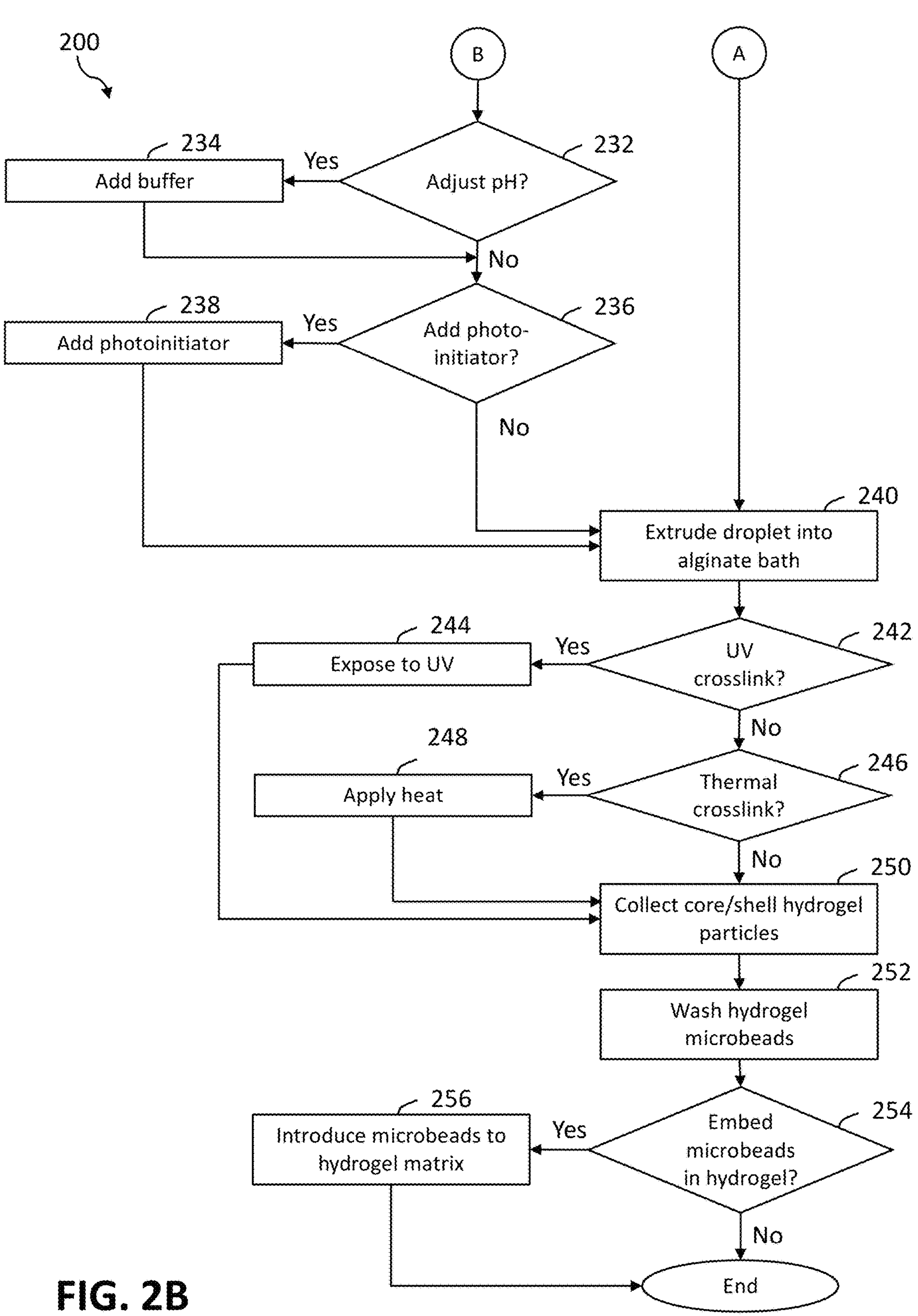

With reference now to FIGS. 2A and 2B, there is shown an exemplary method 200 for preparing therapeutic agent containing hydrogel microbeads. The method 200 begins with the separate, and possibly simultaneous, preparation of the hydrogel precursor solution at step 202 and preparation of the alginate bath at step 222. At step 202, preparation of the hydrogel precursor solution begins with provision of the hydrogel precursor solution base or solvent system. In the embodiments disclosed herein, the hydrogel precursor solution base is water. The water base may be type I water (i.e., ultrapure water), type II water, type III water, deionized water, distilled water, type IV water, any combination thereof, or any water of comparable purity. In some embodiments, the hydrogel precursor solution may be a non-toxic, biocompatible, polar solvent.

At decision diamond 204, a determination is made whether to adjust the viscosity of the hydrogel precursor solution. In various embodiments, the viscosity of the hydrogel precursor solution is from about 1 up to about 500 cP. In some embodiments, the viscosity of the hydrogel precursor solution is about 100 cP at room temperature. The relative viscosity of the hydrogel precursor solution and the alginate bath is critical for formation of core/shell microparticles. As discussed below, the viscosity of the hydrogel precursor solution should be greater than the viscosity of the alginate bath. Where the determination is made to adjust the viscosity of the hydrogel precursor solution, the method 200 proceeds to step 206 where a viscosity modifier is added to the hydrogel precursor solution. The viscosity modifier may include PEG, carboxymethyl cellulose, xanthan gum, or mixtures thereof. Where the determination is made not to adjust the viscosity of the hydrogel precursor solution, the method 200 proceeds to decision diamond 208.

At decision diamond 208, a determination is made whether to adjust the density of the hydrogel precursor solution. Where the determination is made to adjust the density of the hydrogel precursor solution, the method 200 proceeds to step 210 where a density modifier is added to the hydrogel precursor solution. The density modifier may include iodixanol, ficoll, or combinations thereof. Where the determination is made not to adjust the density of the hydrogel precursor solution, the method 200 proceeds to decision diamond 212.

At decision diamond 212, a determination is made whether to adjust the pH of the hydrogel precursor solution. Where the determination is made to adjust the pH of the hydrogel precursor solution, the method 200 proceeds to step 214 where a buffer is added to the hydrogel precursor solution. The buffer may include histidine, 4-(2-hydroxyethyl)-1-piperazineethanesulfonic acid (HEPES), and combinations thereof. Where the determination is made not to adjust the pH of the hydrogel precursor solution, the method 200 proceeds to step 216.

At step 216, a hydrogel precursor compound is added to the hydrogel precursor solution. In some embodiments, the hydrogel precursor compound may be included in the solution system at concentrations from about 0.4% to 4.0% w/v (i.e., 4-40 mg/mL), based upon the total volume of the solution. In some embodiments, hydrogel precursor compound may be included in the solution system at concentrations from about 1-50% w/w, based upon the total weight of the solution. The hydrogel precursor compound is a non-alginate biocompatible hydrogel-forming polymer, oligomer, and/or monomer that is capable of forming a crosslinked matrix (i.e., hydrogel) through polymerization and/or crosslinking. In some embodiments, the hydrogel precursor compounds are functionalized hydrogel-forming polymers, oligomers, and/or monomers having a backbone that has been chemically modified to include one or more of a plurality of chemically reactive groups (i.e., functional groups) capable of forming covalent or ionic bonds (i.e., crosslinks) to form the hydrogel matrix. Exemplary hydrogel precursor compounds include: branched or unbranched hyaluronic acid (HA), branched or unbranched functionalized HA (also termed modified hyaluronic acid), branched or unbranched polyethylene glycol (PEG), branched or unbranched functionalized PEG, non-alginate polysaccharide, collagen, gelatin, chitosan, and agarose. Glycosil® and HyStem®-C are commercially available functionalized HAs. Glycosil® and HyStem®-C are thiolated hyaluronan or thiol-modified HA, generally termed "ThHA" herein. Other functionalized HAs include methacrylated hyaluronic acid (MeHA), acrylated hyaluronic acid (AHA), pentenoate hyaluronic acid (PHA), and norbornene hyaluronic acid (NorHA). Examples of functionalized PEG include PEG diacrylate (PEGDA). Examples of functionalized branched PEG include 4 or 8-arm PEG maleimide (PEGMAL), 4 or 8-arm PEG vinyl sulfone, and 4 or 8-arm PEG acrylate. Examples of functionalized collagen include thiolated collagen (collagen-SH).

In some embodiments, the hydrogel precursor compound is multiple hydrogel polymer precursor compounds. In various embodiments, the hydrogel precursor compounds are methacrylate modified hyaluronic acid, also termed methacrylate hyaluronic acid (MHA), and sodium hyaluronate.

The method 200 proceeds to step 218 where one or more divalent cation is added to the hydrogel precursor solution. The divalent cation may include $Ca^{2+}$, $Ba^{2+}$, $Sr^{2+}$, or combinations thereof. In various embodiments, the divalent cation is added to the hydrogel precursor solution so that the divalent cation concentration in the hydrogel precursor solution ranges from about 0.025 mol/L to about 0.25 mol/L. The divalent cation is added to the hydrogel precursor solution as a water-soluble ionic salt with a water-soluble anion, such as Chloride. It is critical that the water-soluble anion not be a chelator.

The method 200 proceeds to step 220 where one or more therapeutic agent is added to the hydrogel precursor solution. The therapeutic agent may be, without limitation, a hormone (e.g., estradiol, testosterone, bioidenticals, or any of the hormones described above), opioids, numbing agents, and competitive antagonists in metabolic pathways. In some embodiments, the therapeutic agent is added to the hydrogel precursor solution in amounts yielding a hydrogel precursor solution that is 1-50% therapeutic agent by mass.

All of steps 206, 210, 214, 216, 218, 220, and decision diamonds 204, 208, and 212 need not be performed only in the order presented above, but may be performed in any order, some of the steps may be performed simultaneously, or all of the steps may be performed simultaneously.

In an illustrative embodiment, the hydrogel precursor solution comprises a mixture of hyaluronic acid, a divalent cation, and estradiol.

Separately, the alginate bath is prepared in step 222, where an open topped container is used to receive a solution of alginate in water. The alginate may be added as sodium alginate or other alginate salts (excluding salts with calcium, strontium, or barium). Various types of gel-forming, but decrosslinkable, alginates can be used, such as low viscosity/low molecular weight and high-G alginates are preferred, such as those extracted from *Laminaria* hyperborean. The amount of alginate in the solution can be varied from 0.1% to about 2.0% w/v, based upon the total volume of the alginate bath taken as 100%. The water may be type I water (i.e., ultrapure water), type II water, type III water, deionized water, distilled water, type IV water, any combination thereof, or any water of comparable purity. In some embodiments, a non-toxic, biocompatible, polar solvent other than water may be used to prepare the alginate bath. In one illustrative embodiment, the alginate bath is prepared with 0.15% w/v Protanal®.

The viscosity of the alginate bath may generally range from about 1 to about 20 cP. In some embodiments, the viscosity of the alginate bath ranges from about 1 to about 4 cP at room temperature. As discussed above, the ratio of the viscosity of the alginate bath to the viscosity of the hydrogel precursor solution is critical to formation of the core/shell particles. More specifically, the ratio of viscosity of the hydrogel precursor solution to the viscosity of the alginate solution should be greater than 1 at room temperature. Such a ratio of viscosities allows droplets of hydrogel precursor solution to maintain their shape upon contact with the surface of the alginate bath and causes the alginate bath solution to surround the exterior of the hydrogel precursor solution droplet. In some embodiments, the ratio of viscosity of the hydrogel precursor solution to the viscosity of the alginate solution is 25 from about 1:1 to about 1000:1. In some embodiments, the ratio of viscosity of the hydrogel precursor is about 20:1.

The method 200 proceeds to decision diamond 224 where a determination is made whether to add a crosslinking agent to the alginate bath. Exemplary crosslinking agents include PEGDA, dithiothreitol (DTT), PEG dithiol, PEGDA, PEG divinyl sulfone, PEG dimaleimide (MAL-PEG-MAL), and ethylene glycol bismercaptoacetate (BMA). A crosslinking agent is added to the alginate bath at step 226 when the method 200 includes a chemical reaction between the crosslinking agent and the hydrogel precursor compound to crosslink the hydrogel precursor compound and form a hydrogel matrix. In some embodiments, the crosslinking agent is included in the alginate bath at concentrations ranging from 0.5-30 mM. In some embodiments, the crosslinking agent is included in the alginate bath at concentrations ranging from 1-20 mM. In some embodiments, the crosslinking agent is included in the alginate bath at concentrations ranging from 2-15 mM. In some embodiments, the crosslinking agent is included in the alginate bath at concentrations ranging from 2.5-10 mM. In some embodiments, the crosslinking agent is included in the alginate bath at concentrations ranging from 2.5-5 mM. In these embodiments, the crosslinking agent must be selected to correspond, i.e., react, with the hydrogel precursor compound. PEGDA may be used as the crosslinking agent for the following hydrogel precursor compounds: ThHA, collagen-SH, MeHA, and AHA. DTT may be used as the crosslinking agent for the following hydrogel precursor compounds: PHA, NorHA, AHA, branched PEG vinyl sulfone, and branched PEG acrylate. PEG dithiol may be used as the crosslinking agent for the following hydrogel precursor compounds: AHA, PHA, NorHA, branched PEGMAL, branched PEG vinyl sulfone, and branched PEG acrylate. PEG divinyl sulfone or MAL-PEG-MAL may be used as the crosslinking agent for the ThHA hydrogel precursor compound. BMA may be used as the crosslinking agent for the following hydrogel precursor compounds: branched PEG vinyl sulfone and branched PEG acrylate.

The method 200 proceeds to decision diamond 228 where a determination is made whether to adjust the viscosity of the alginate bath. As discussed above, it is critical that the viscosity of the alginate bath be less than the viscosity of the hydrogel precursor solution. Where it is determined that the viscosity of the alginate bath should be adjusted, the method 200 proceeds to step 230.

At step 230 a viscosity modifier is added to the alginate bath to adjust the viscosity of the alginate bath. This adjustment could be to lower the viscosity of the alginate bath or to increase the viscosity of the alginate bath as necessary for formation of core/shell particles. In various embodiments, a viscosity modifier is added to the alginate bath in an amount such that the viscosity modifier is present in the alginate bath at a concentration ranging from 50-500 mM. In some embodiments, the viscosity modifier is mannitol. In one embodiment, mannitol is added in an amount such that it is present in the alginate bath at a 300 mM concentration.

The method 200 proceeds to decision diamond 232 where a determination is made whether to adjust the pH of the alginate bath. The pH of the alginate bath should range from about 6.2 to about 7.8. In some embodiments, the pH of the alginate bath ranges from about 6.6 to about 7.4. Where the determination is made to adjust the pH of the alginate bath to conform to the pH ranges identified above, the method 200 proceeds to step 234 where a buffer is added to the alginate bath.

In one embodiment of step 234, the pH of the alginate bath is adjusted to pH 7.6 using a 15 mM N-(2-Hydroxyethyl) piperazine-N'-2-ethanesulfonic acid (HEPES) buffer.

The method 200 proceeds to decision diamond 236 where a determination is made whether to add a photoinitiator to the alginate bath. In embodiments where ultraviolet light is used to crosslink the hydrogel precursor compounds, the determination to add a photoinitiator to the alginate bath may be made and the method 200 proceeds to step 238. Where the determination is made not to add a photoinitiator to the alginate bath, the method 200 proceeds to step 240.

At step 238, a photoinitiator is added to the alginate bath. In some embodiments, the photoinitiator is dissolved into the alginate bath. In some embodiments, the photoinitiator comprises a solution, which solution is added to the alginate bath. In one embodiment, the photoinitiator is Lithium phenyl-2,4,6-trimethylbenzoylphosphinate (LAP). In one embodiment, the photoinitiator is a solution of LAP in water.

Upon generation of the hydrogel precursor solution in steps 202-220 and generation of the alginate bath in steps 222-238, the method 200 proceeds to step 240 where droplets of the hydrogel precursor solution are extruded into the alginate bath. In some embodiments, the alginate bath is stirred while the hydrogel precursor solution droplets are extruded. As discussed above, since the viscosity of the hydrogel precursor solution is greater than the viscosity of the alginate bath, the droplets of hydrogel precursor solution maintain their shape upon contact with the surface of the alginate bath and the alginate bath solution surrounds the exterior of the hydrogel precursor solution droplet. The average diameter of the extruded droplets ranges from 100 μm-1400 μm. In this context, "average" may refer to the arithmetical mean or to the arithmetical median. In some embodiments, the average diameter of the extruded droplets ranges from 600 μm-1100 μm. In narrower embodiment, the average diameter of the extruded droplets ranges from 150 μm-500 μm.

The presence of the divalent cation in the hydrogel precursor solution droplet causes alginate in the alginate bath surrounding the droplet to agglomerate to the surface of the droplet and crosslink around the droplet as the cations leach from the hydrogel precursor solution droplet. This effectively traps the un-crosslinked hydrogel precursor solution (including the therapeutic agent) within a shell of crosslinked alginate, forming core shell microparticles. Each core shell microparticle has a crosslinked outer alginate shell and an inner liquid core of the hydrogel precursor solution.

Upon formation of the core shell microparticles, a determination is made at decision diamond 242 whether to expose the hydrogel core of the core shell microparticles to activating radiation, such as ultraviolet (UV) radiation, for the purpose of crosslinking the hydrogel core. The determination to expose the hydrogel core to UV radiation is made when the hydrogel precursor compound or the combination of the hydrogel precursor compound and the crosslinking agent require UV radiation to initiate formation of the hydrogel matrix through crosslinking. Exemplary hydrogel precursor compounds that may be crosslinked by exposure to UV radiation include: MeHA, AHA, PEGDA, PEG diacrylamide, branched PEGMAL, branched PEG vinyl sulfone, and branched PEG acrylate. Exemplary combinations of a hydrogel precursor compound and a crosslinking agent that may be crosslinked by exposure to UV radiation include: MeHA+PEGDA, AHA+PEGDA, PHA+DTT, PHA+PEG dithiol, NorHA+DTT, and NorHA+PEG dithiol. In these embodiments, the method 200 proceeds to step 244 where the core shell microparticles, specifically the hydrogel core of the core shell microparticles, are exposed to UV light to crosslink the hydrogel core and form core shell crosslinked microparticles.

In one embodiment, the hydrogel precursor solution includes methacrylated hyaluronic acid (MHA) and sodium hyaluronate, while the alginate bath includes LAP. In this embodiment, the determination is made at decision diamond 242 to expose the core shell microparticles to UV light at step 244.

At step 244, the core shell microparticles are exposed to UV light continuously for 1-35 minutes to crosslink the hydrogel core of the core shell microparticles and form core shell crosslinked microparticles. In some embodiments, the core shell microparticles are exposed to UV light continuously for 0.5-5 minutes. In some embodiments, the core shell microparticles are exposed to UV light continuously for 0.5-10 minutes. In some embodiments, long-wave UV light, such as that emitted by a PortaRay 400 from Uvitron International, initiates radical photopolymerization of the hydrogel precursor compound. As disclosed herein, long-wave UV light has a wavelength from 100-400 nm, UVA light has a wavelength from 315-400 nm, and UVB light has a wavelength from 280-315 nm.

In one embodiment, the UV radiation applied to the core shell microparticles generated in step 240 are identified in Table 1.

TABLE 1

| Process Controls for Core Crosslinking |
|---|
| 1 mW/cm$^2$ < UVA intensity < 15 mW/cm$^2$ |
| 0 mW/cm$^2$ < UVB intensity < 0.5 mW/cm$^2$ |
| 0.5 min < $UV_{A\ or\ B}$ exposure time < 5 min |

In practice, the crosslinking agent(s) in the alginate bath filter or leach through the alginate shell formed around a hydrogel core to access the hydrogel in the core and thereby initiate crosslinking when UV radiation is applied. Upon completion of crosslinking to form the hydrogel matrix in step 244, the method 200 proceeds to step 250 where crosslinked core/shell hydrogel particles are collected.

Where the determination is made at decision diamond 242 that the hydrogel precursor compound or the combination of hydrogel precursor compound and crosslinking agent are not amenable or capable of UV-initiated crosslinking, the method 200 proceeds to decision diamond 246. At decision diamond 246, a determination is made whether to crosslink the hydrogel precursor compound or combination of hydrogel precursor compound and crosslinking agent with a thermally mediated crosslinking mechanism. The determination to heat the alginate bath, and therefore the core/shell particle, to advance or initiate crosslinking of the hydrogel is made when the hydrogel precursor compound or the combination of the hydrogel precursor compound and crosslinking agent crosslink through a chemical reaction, instead of UV-mediated crosslinking. Exemplary combinations of hydrogel precursor compounds and crosslinking agents that may be chemically crosslinked include: AHA+DTT, AHA+PEG dithiol, ThHA+PEGDA, ThHA+PEG divinyl sulfone, ThHA+PEG dimaleimide, branched PEGMAL+DTT, branched PEGMAL+PEG dithiol, branched vinyl sulfone+DTT, branched vinyl sulfone+PEG dithiol, branched vinyl sulfone+ethylene glycol BMA, branched PEG acrylate+DTT, branched PEG acrylate+PEG dithiol, branched PEG acrylate+ethylene glycol BMA, and collagen-SH+PEGDA. In these embodiments, the method 200 may proceed to step 248 where additional heat is applied to the alginate bath containing the core/shell particles to crosslink the hydrogel core and form core/shell crosslinked microparticles. In practice, the crosslinking agent(s) in the alginate bath filter or leach through the alginate shell formed around a hydrogel gel core to access the hydrogel in the core and are thereby available to crosslink the hydrogel precursor compound, such as when heat is applied, to form the core/shell crosslinked microparticles. Where the determination is made at decision diamond 246 that the combination of hydrogel precursor compound and crosslinking agent do not require additional heat to form the crosslinked hydrogel matrix, the method 200 proceeds to step 250 where core/shell crosslinked hydrogel particles are collected from the alginate bath.

In some embodiments, no heat or UV radiation is required to crosslink the hydrogel precursor compound with the crosslinking agent. In these embodiments, the crosslinking agent(s) in the alginate bath filter or leach through the alginate shell formed around a hydrogel gel core to access the hydrogel in the core and thereby initiate crosslinking with the hydrogel precursor compound through a chemical reaction. In these embodiments, the core/shell particles are allowed to remain in the alginate bath for 1-30 minutes so that the crosslinking agent(s) in the alginate bath leach through the outer alginate shell of the core/shell particles to access and crosslink the core hydrogel precursor compound to form core/shell crosslinked microparticles. It has been found that up to 3.4 kDalton PEGDA crosslinking molecules are capable of passing through alginate shells to reach and crosslink liquid hydrogel cores within. Thus, in these embodiments, extrusion of the hydrogel droplet into the alginate bath in step 240 is also a crosslinking step. Exemplary combinations of hydrogel precursor compounds and crosslinking agents that may be chemically crosslinked include: AHA+DTT, AHA+PEG dithiol, ThHA+PEGDA, ThHA+PEG divinyl sulfone, ThHA+PEG dimaleimide, branched PEGMAL+DTT, branched PEGMAL+PEG dithiol, branched vinyl sulfone+DTT, branched vinyl sulfone+PEG dithiol, branched vinyl sulfone+ethylene glycol BMA, branched PEG acrylate+DTT, branched PEG acrylate+PEG dithiol, branched PEG acrylate+ethylene glycol BMA, and collagen-SH+PEGDA. Upon completion of crosslinking to form the hydrogel matrix in this step 240, the method 200 proceeds directly to step 250 where crosslinked core/shell hydrogel particles are collected.

During the crosslinking gelation of the hydrogel precursor compound or the combination of the hydrogel precursor compound and crosslinking agent, therapeutic agents in the hydrogel precursor solution may be retained, suspended, entrapped, and/or encapsulated within the interstitial spaces or pores of the resulting gelled matrix structure. This gelled matrix structure of the hydrogel is a 3-dimensional matrix that is characterized as a porous elastic solid, wherein elastic deformation is reversible. Resulting microsphere microparticles formed from such gelled matrix are semi-rigid, resilient, and can flex under a load, then return to its original shape upon removal of the load. Although resilient and elastic, the hydrogel microparticles disclosed herein may fracture or break into smaller pieces under application of sufficient force. Since the hydrogel microparticles are irreversible hydrogels, the matrix crosslinks will not reform or otherwise recover or self-heal. The hydrogel microparticles disclosed herein have both mean and median diameters (or surface-to-surface dimension if appropriate) ranging from 100 to 1400 μm.

At step 250, the core shell crosslinked microparticles are collected from the alginate bath by straining, sieving, or filtering. A steel mesh screen or comparable filtering implement may be used to collect the core/shell particles from the alginate bath.

The collected core shell microparticles are then transformed into hydrogel microbeads by the removal of the outer alginate shell at step 252. Removal of the outer alginate shell may be done by contacting the collected core/shell particle(s) with a chelating agent and/or physically agitating the collected core/shell particles. Chelating agents used to remove the alginate shell may include citrate (e.g., sodium citrate), ethylenediaminetetraacetic acid (EDTA), egtazic acid (EGTA), phosphates (e.g., orthophosphate, phosphate salts, etc.), and mixtures thereof. In practice, the collected core/shell particles are washed with a buffer solution containing a chelating agent to remove the alginate shell. In some embodiments, the buffer solution is Dulbecco's phosphate buffer solutions (DPBS). This washing may include stirring or agitation of the buffer solution. Stirring or agitation may be provided through magnetic stir bars and stir plates, or sonicators that may physically break up the outer alginate shell of the core/shell crosslinked microparticles. In some embodiments, the collected core/shell particles are washed with chelating agents, by stirring the core/shell particles in a solution of the chelating agents (wash solution) for 1-30 minutes. In some embodiments, core/shell particles are washed in the wash solution for 5-20 minutes. In some embodiments, this washing step 252 may include repeated washing where the core/shell particles are collected from the first buffer (washing) solution used to wash them and subjected to a second washing in a second buffer solution that may be of the same composition as the first washing solution. In these embodiments, the concentration of the chelating agent in the first wash solution and the second wash solution may be the same. However, in these embodiments, the concentration of chelating agent in the first wash solution may be less than the concentration of chelating agent in the second wash solution. The washing buffer solution may include the chelating agent at a concentration of 10-100 mM. In some embodiments, the buffer solution may include the chelating agent at a concentration of 25-50 mM. After one or more washings, shell-less therapeutic agent containing hydrogel matrix microbeads may be collected (i.e., by filtering) for later use or further processing.

At decision diamond 254, a determination is made whether to suspend the washed hydrogel microbeads from step 252 in a hydrogel matrix, such as a gel, paste, or cream. The determination to suspend the washed hydrogel microbeads in a hydrogel matrix in step 256 may be made where the hydrogel microbeads are not intended to be injected sub-dermally.

The hydrogel matrix in which the hydrogel microbeads are suspended may be formed from any of the hydrogel precursor compounds and crosslinking agents described above. The method 200 terminates with either the collection of washed hydrogel microbeads that are free from any substantial amount of alginate or with suspension of the washed hydrogel microbeads in a hydrogel matrix.

Example Microsphere Generation and Analysis

All percentages in the examples below are weight to weight (e.g., weight of component to weight of a solution or composition). Abbreviations for the terms used to describe the examples, as well as test articles and equipment information are listed below in Table 2.

TABLE 2

| Abbreviation or Term | Definition/Explanation |
| --- | --- |
| 3D | 3 Dimensional |
| API | Active Pharmaceutical Ingredient |
| CSS | Core Shell Spherification |
| E2 | Estradiol |
| E2 + hydrogel | Encapsulated Estradiol |
| ELISA | Enzyme-Linked Immunosorbent Assay |
| HA | Hyaluronic Acid |
| HRT | Hormone Replacement Therapy |
| SOP | Standard Operating Procedure |
| T | Testosterone |

| Test Article | Batch No. | Description | Source |
| --- | --- | --- | --- |
| Non-micronized Estradiol | SLCQ6890 | Beta-estradiol, powder | Sigma Aldrich |
| Micronized Estradiol | 203203/G | Estradiol hemihydrate, powder | Medisca |
| Sodium alginate | BP-1905-07 | ProNova ™ UP LVG | Nova Matrix |
| Hyaluronic acid | 9003 | powder | Advanced Biomatrix |

| Reagent/Equipment | Manufacturer |
| --- | --- |
| Personal Protective Equipment, various | Various |
| E2 ELISA | R&D Systems |
| Water Bath, IsoTemp 220 | Fisher Scientific |
| Biosafety Cabinet | Labconco |
| Centrifuge, 5810R | Eppendorf |
| Cytation 5 Imaging Reader | Biotek/Agilent |
| CSS Encapsulator | Likarda |
| Semi-Micro calibrated viscometer | Cannon-Manning |

Exemplary Formation of E2 into Microspheres

A formulation optimized by the experiments described above was used to create E2-containing hydrogel microspheres. E2 was used as a proxy for testosterone. Briefly, the precursor solution of HA, E2, and $Ca^{2+}$ was extruded through the Likarda CSS instrument using a stirring bath of sodium alginate containing mannitol. A 400 μm diameter inner fluid nozzle was used within a 1.5 mm concentric air nozzle. The droplets were extruded into the stirring alginate bath solution using compressed nitrogen.

After irradiation to initiate the polymerization of the hydrogel droplet, the alginate shell was removed by rinsing in a 25 mM citrate buffer for 5 min while stirring to dissolve the alginate shell. The resulting shell-less microspheres were collected using a steel mesh screen and underwent a second rinsing with the 25 mM citrate buffer.

Release assays on the E2 microspheres were conducted in the same manner as described above for the discs.

Imaging of Microspheres

When imaging the microspheres, the spheres were placed in clear-bottomed 96 well plates and imaged with a Cytation 5 Biotek Microplate reader. Diameter measurements were collected using ImageJ software.

Statistical Analysis

Statistical analysis, including one-way Analysis of Variance and T-tests, was performed on collected data using SigmaPlot 13.0 software. Statistical significance was defined as $P<0.050$.

The results indicate that encapsulation was successful in creating an extended-release composition for E2. The results of each study are summarized below.

Viscosity Measurement

The precursor viscosity measurements were collected using a Cannon-Manning Semi-Micro calibrated glass capillary viscometer at room temperature.

Confirm HA Hydrogel Encapsulation of E2 Powder

Figure 3A:
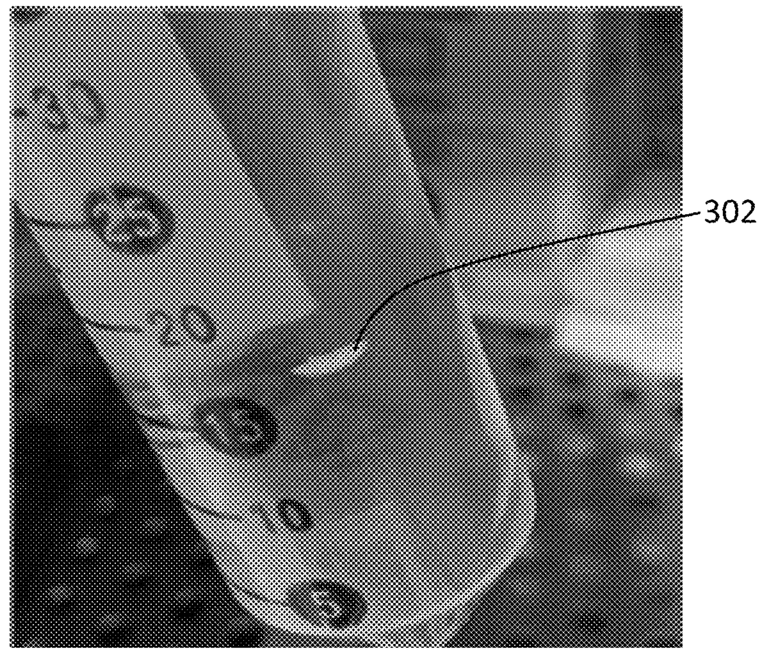
FIG. 3A shows an example of a single E2 disc in a tube of incubation media.
Figure 3B:
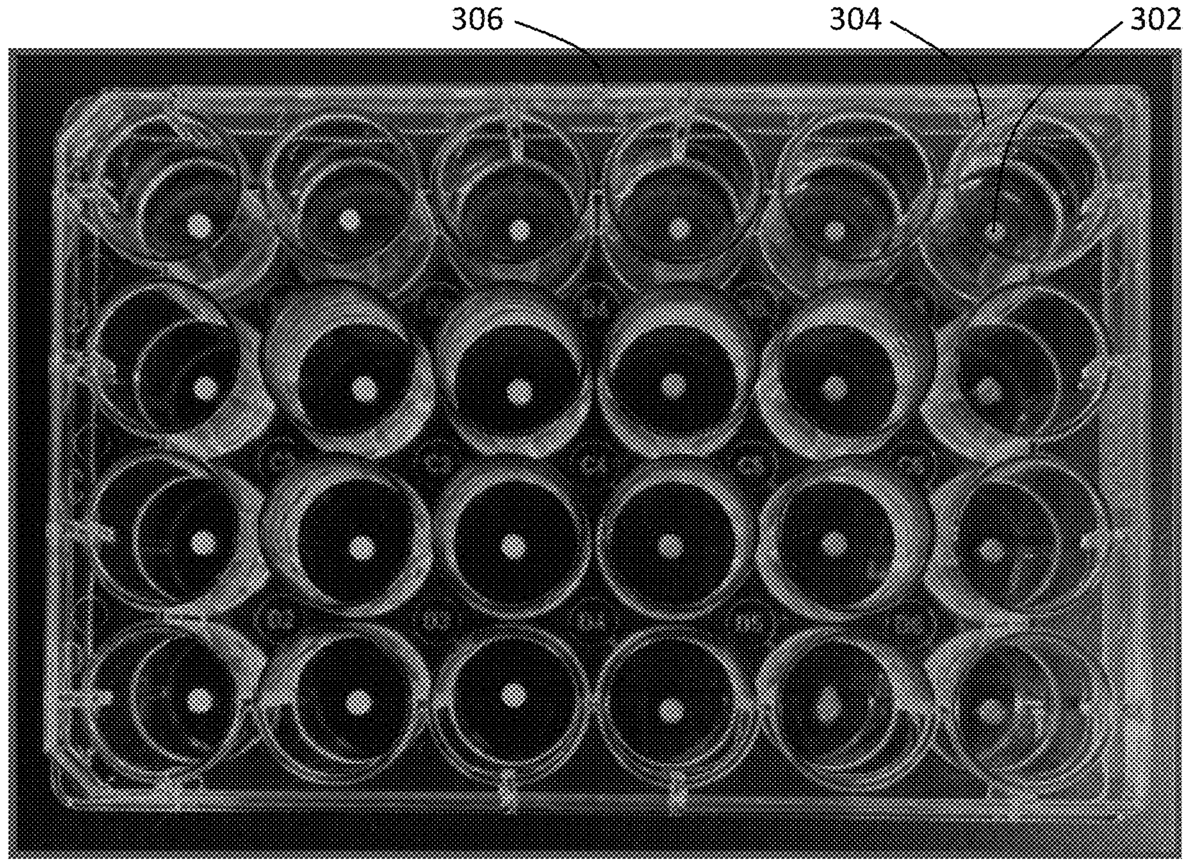
FIG. 3B illustrates the organization of 1 disc per well for the single release assay.

E2 powder was encapsulated into bulk HA discs to determine whether the powder form could be trapped within an aqueous hydrogel. FIG. 3A shows an example of a single E2 disc 302 in a test tube vial. FIG. 3B illustrates the organization of 1 disc 302 per well 304 of a 48 well plate 306 for the release assays.

A range of estradiol (E2) powder concentrations were encapsulated in bulk hyaluronic acid discs, each disc formed from 1% HA by mass in the hydrogel precursor compound solution. Mass measurements were collected at the time of manufacturing and on day 7. The various E2 powder concentration specifications for exemplary hydrogel are listed below in Table 3.

TABLE 3

| Embodiment # | E2 mass fraction | HA mass fraction |
|---|---|---|
| 1 | 0.25 | 1 |
| 2 | 0.50 | 1 |
| 3 | 1.00 | 1 |
| 4 | 10 | 1 |
| 5 | 20 | 1 |
| 6 | 30 | 1 |
| 7 | 40 | 1 |
| 8 | 45 | 1 |
| 9 | 50 | 1 |

E2 Hydrogel Release Profile Measurements

The release of E2 from hydrogel discs was measured on four (4) disc samples described below in Table 4.

TABLE 4

| Embodiment | E2 mass fraction (%) | HA mass fraction (%) | Disc size (μL) |
|---|---|---|---|
| A | 15% | 1% | 20 |
| B | 30% | 2% | 20 |
| C | 30% | 1% | 10 |
| D | 30% | 1% | 20* |

*20 μL disc in 100 U/mL hyaluronidase solution

Positive control samples for comparison to hydrogel discs were comprised of 6 mg E2 pellets as well as 6 mg of raw E2 powder. All samples were incubated in 120 mg E2/L of incubation medium. 30% E2 equates to 6 mg of E2 powder per droplet. Gels were rinsed 5 times using incubation medium to remove loosely bound E2 particles from the exterior of the hydrogel discs prior to their addition to the incubation bath.

All samples were incubated in 50 mL incubation medium in 50 mL centrifuge tubes at 37° C. while rotating at 6 rpm.

At specific time points (days 1, 2, and 3), aliquots of the incubation media were removed and assayed for the amount of free E2 using ELISA. Samples were diluted 400-fold to 1225-fold using a calibrator dilutant and tested. Low standards were removed from the analysis. For micronized estriol (E3), the samples were diluted 1800-fold.

E2 Hydrogel Release Profile

Figure 4:
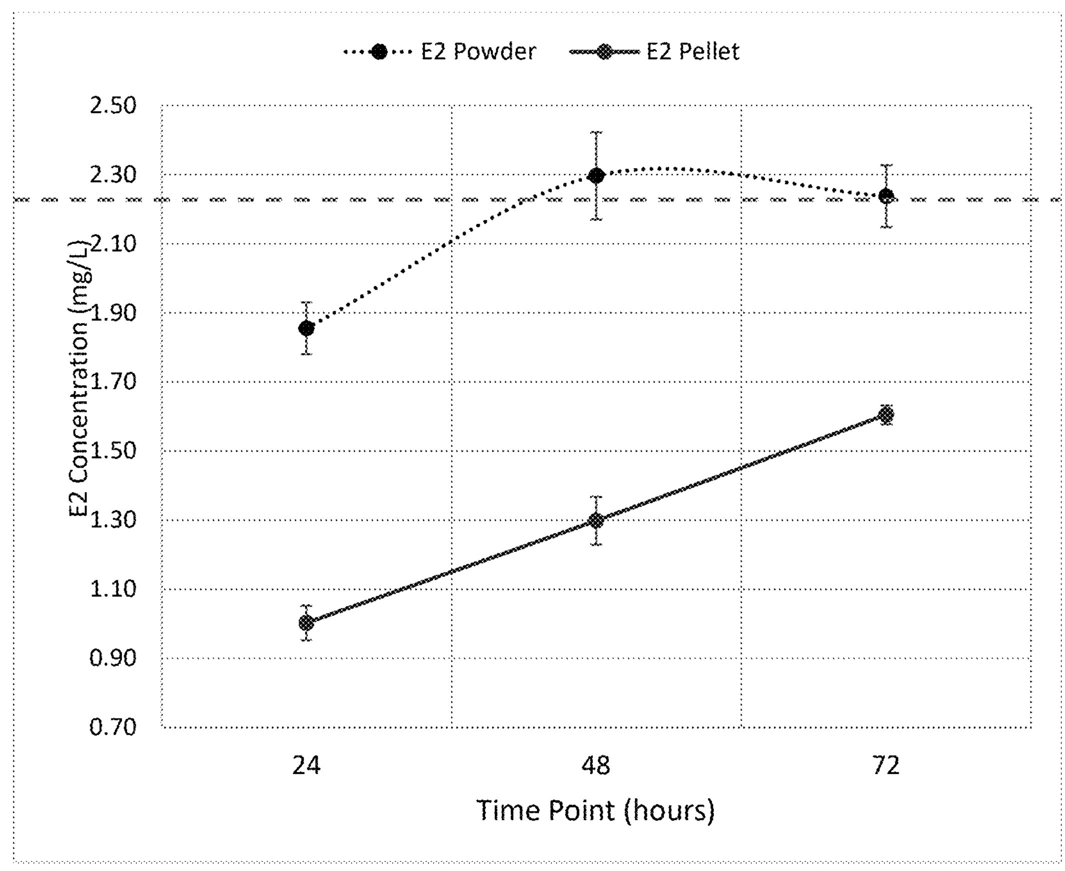
FIG. 4 shows a release profile of control samples.

Optimization of the hydrogel formulation as a carrier for E2 was completed by comparing the release profile of an E2 pellet. FIG. 4 illustrates the release profiles of the controls—E2 pellets and free E2 powder. The dotted line at about 2.25 mg/L indicates the solubility limit of E2 in the study buffer. Free E2 powder released E2 into the incubation media at a concentration of about 1.85 mg/L by day 1, then reached the saturation point of the incubation media by day 2 and maintained the saturation point concentration for the day 3 measurement. In contrast, the E2 pellet displayed an approximately linear release profile of about 0.3 mg/L/day for days 1-3, after an initially greater rate from day 0-1 (about 1.0 mg/L/day). Thus, by day 3, the E2 pellet had released an accumulated concentration of about 1.60 mg/L of E2 into the study buffer.

Figure 5:
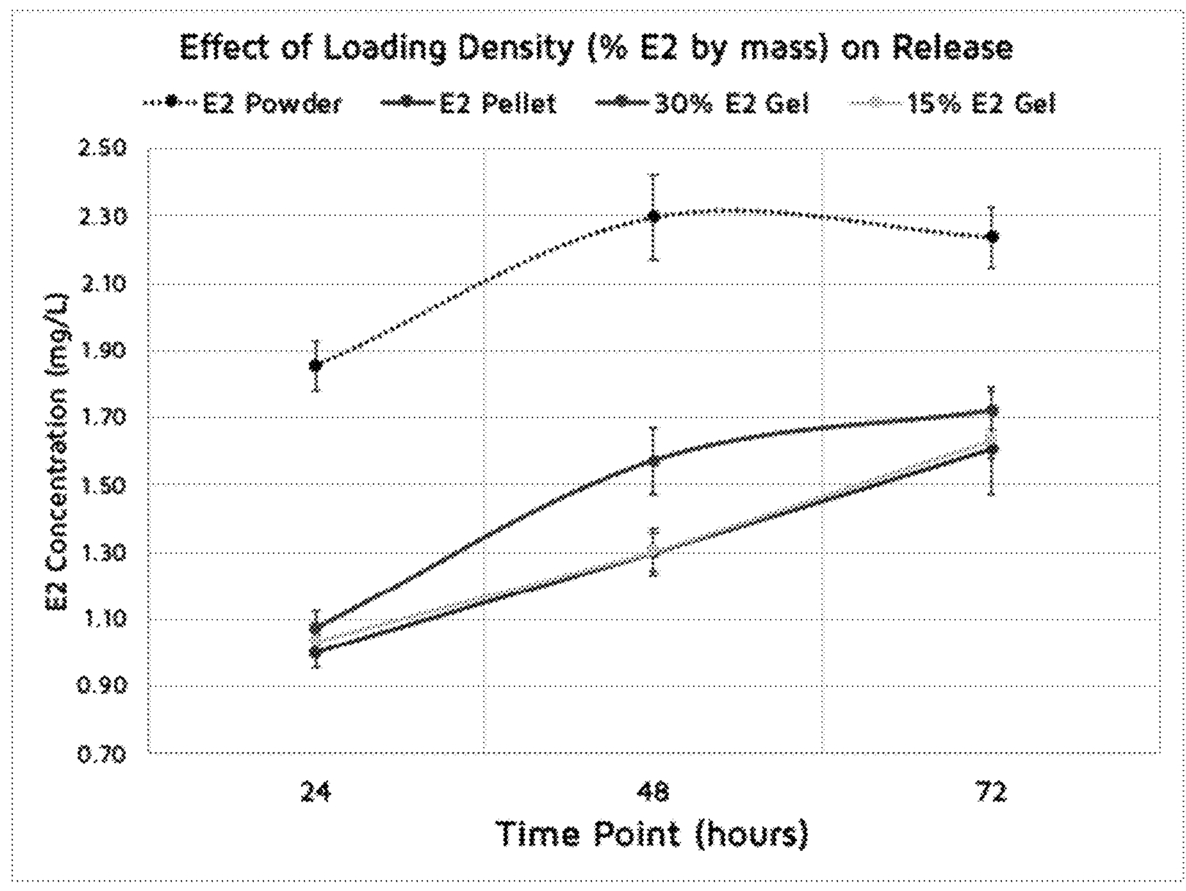
FIG. 5 shows an effect of E2 loading density within the discs.

The effect of the loading density of the E2 (15% versus 30% E2 by mass) is shown in FIG. 5. In FIG. 5, the HA discs are 20 μL and 1% HA by mass. The initial release concentration from day 0-1 for the encapsulated 30% E2 disc and the encapsulated 15% E2 disc were statistically indistinguishable (about 1.05 mg/L). And, as expected, the higher loading density of the encapsulated 30% E2 had a higher release rate over time than the encapsulated 15% E2 disc. The encapsulated 30% E2 had an average release rate for days 1-3 of about 0.33 mg/L/day, with a peak release rate for days 1-2 of about 0.55 mg/L/day, reaching an accumulated release concentration on day 3 of about 1.70 mg/L. In contrast, the encapsulated 15% E2 discs had a release profile that was statistically indistinguishable from the E2 pellet control sample. These release values were deemed non-erroneous as they were still significantly less than the release rate of the free E2 powder positive control.

Samples in which E2 loading densities of 50% were attempted resulted in precursor mixtures that were too thick to manufacture into discs and did not mix homogenously. While 40% E2 loading density mixtures were able to form discs, they yielded an uneven mixture of the active ingredient (E2).

Figure 6:
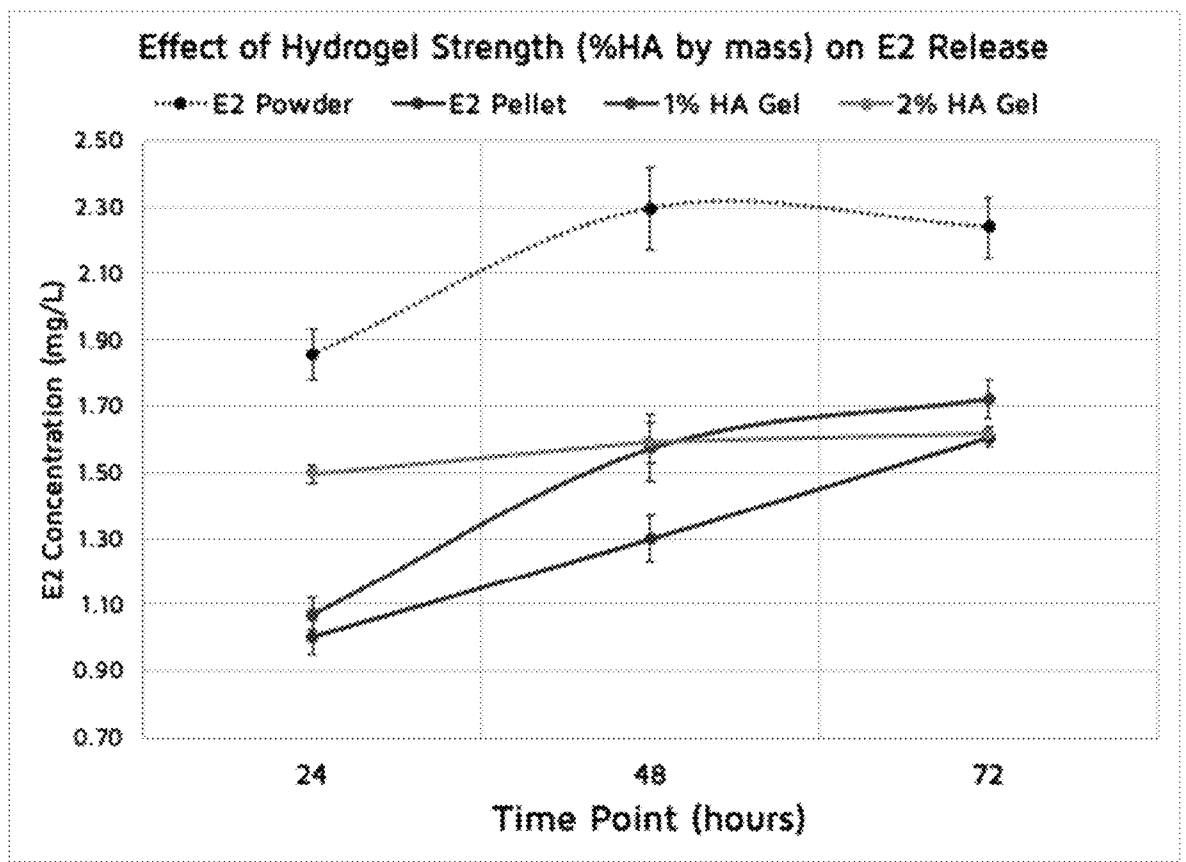
FIG. 6 shows an effect of HA mass on release of E2.

The effect of the HA concentration in the hydrogel was compared in FIG. 6. In FIG. 6, the HA discs are 20 μL with 30% E2 are compared to 1% and 2% mass HA. The gel with a higher concentration of HA (2%) had a greater initial release of E2 (about 1.50 mg/L) than the lower concentration of HA (1%) within 24 hours of formation, which had an initial E2 release of about 1.0 mg/L of E2 for the first 24 hours. But at 72 hours, the release rate from the lower concentration HA disc increased to that of the higher concentration HA disc, both being about 1.60 mg/L/day, which matched the E2 pellet release levels. However, the 1% HA hydrogel better mimicked the E2 pellet release profile, being statistically indistinguishable from the pellet release levels at 24 hours (about 1.0 mg/L), being somewhat higher than the E2 pellet release levels at 48 hours (about 1.60 mg/L compared to the E2 pellet's about 1.30 mg/L), and being only marginally higher than the E2 pellet's release level by 72 hours (about 1.70 mg/L compared to the E2 pellet's about 1.60 mg/L).

Figure 7:
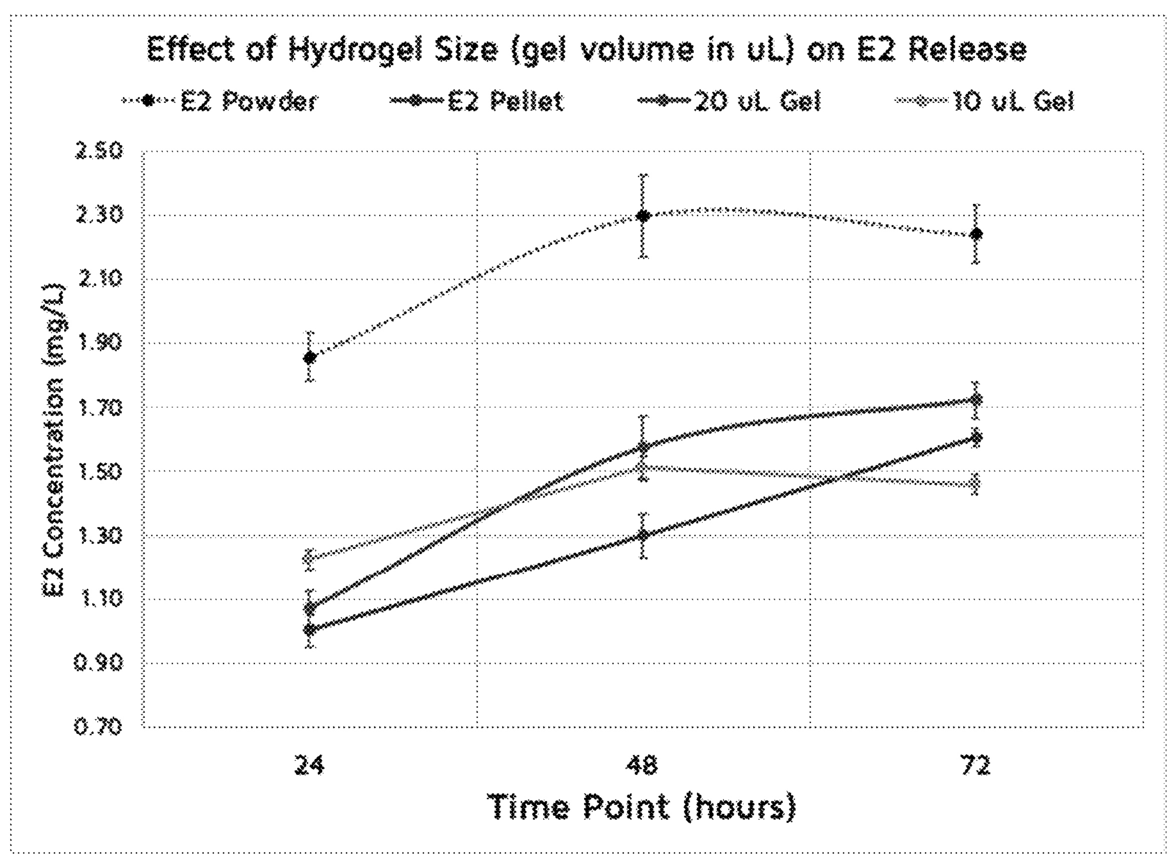
FIG. 7 shows an effect of disc surface area on the release of E2.

Before moving to microspheres, it was important to determine whether size of the disc and thus the surface area had an effect on the release profile as microspheres may have a significantly higher surface area than both the HA discs and the E2 pellets. FIG. 7 summarizes the results of the size study for 1% HA discs loaded with 30% E2. The larger 20 μL HA disc displayed an E2 release level at 24 hours that more closely resembled that of the E2 pellet at about 1.0 mg/L than did the smaller 10 μL HA disc, which displayed an E2 release level at 24 hours of about 1.20 mg/L. However, the larger disc showed a much a greater increase in release of E2 than did the smaller HA disc, reaching about 1.60 mg/L concentration of released E2 at 48 hours, while the smaller HA disc only reached about 1.50 mg/L of released E2 in the same amount of time. Lastly, the smaller HA disc had lower E2 release levels (about 1.45 mg/L E2) than both the E2 pellet (about 1.60 mg/L E2) and the larger HA disc (about 1.70 mg/L E2) at 72 hours. Thus, the smaller disc showed a lower release level at 72 hours and appeared to better match the long-term E2 release profile of the E2 pellet, which is a positive outcome.

In a subject's body, the crosslinks within the HA could be broken by endogenous hyaluronidase. Thus, it was important to assess how adding hyaluronidase to the media would change the release profile. The exposure of the disc to hyaluronidase in an in vitro study is much higher than would be seen in a subject's body. The presence of hyaluronidase increased the release and detection of E2, indicating that the E2 will be released in a functional form in the presence of a subject body's hyaluronidase. The results are shown in FIG. 8.

Figure 8:
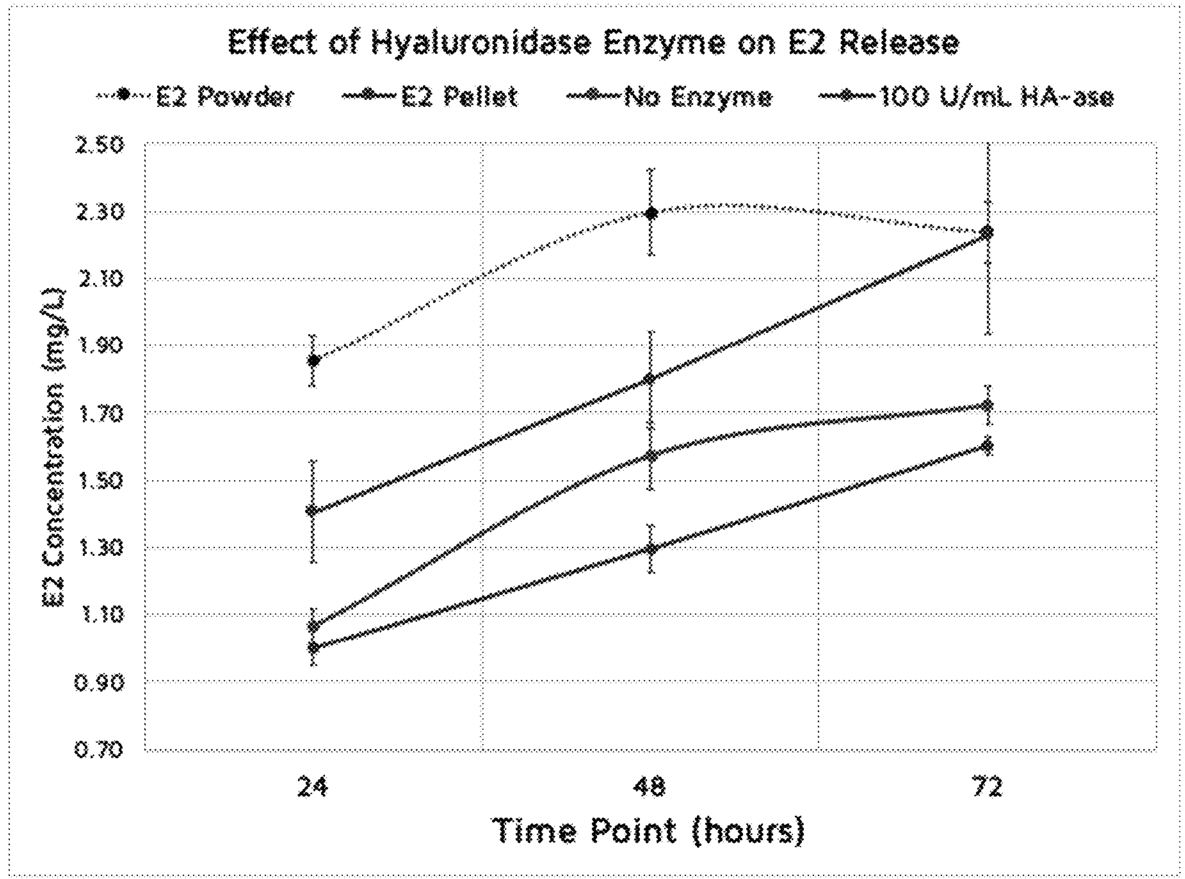
FIG. 8 shows an effect of hyaluronidase on the release of E2.

FIG. 8 shows the E2 release profile 20 μL 1% HA discs loaded with 30% E2 in the presence and absence of hyaluronidase. Hyaluronidase greatly increased the release of E2 from the HA disc, both initially and continually through the 3-day testing period. While both the E2 pellet control sample and the hyaluronidase-free HA disc sample released about 1.0 mg/L E2 at 24 hours, the HA disc in the presence of hyaluronidase released about 1.4 mg/L E2 at 24 hours. Similarly, at 48 hours, although the hyaluronidase-free HA disc sample released more E2 than the E2 pellet, reaching about 1.6 mg/L E2 in the incubation medium, this was much lower than the hyaluronidase exposed sample. The HA disc in the presence of hyaluronidase released up to about 1.8 mg/L E2 at 48 hours. Lastly, unlike the E2 pellet control sample or the hyaluronidase-free HA disc sample, the HA disc in the presence of hyaluronidase released E2 into the incubation medium that reached the E2 saturation level of about 2.25 mg/L.

Figure 9:
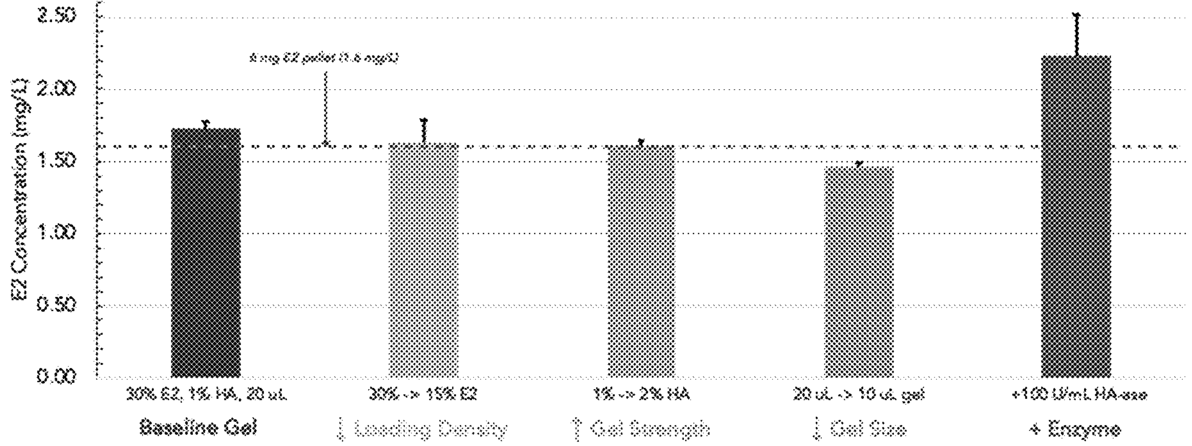
FIG. 9 summarizes optimization experiments and compares them to the rates of E2 release from 6 mg E2 pellets.

FIG. 9 summarizes the results of the studies presented in FIGS. 3-7 where the effect of E2 loading, HA mass %, hydrogel surface area to volume, and the presence of hyaluronidase. The dotted horizontal line shows the level of E2 release exhibited by E2 pellets after 72 hours (about 1.6 mg/L), which is the standard against which the various hydrogel compositions were compared. The leftmost bar represents the E2 release for a 20 μL 1% HA disc loaded with 30% E2 (termed "baseline gel"), about 1.7 mg/L. The next bar to the right represents the E2 release for an HA disc having a lower loading density of E2, reduced from 30% for the baseline gel to 15%, while still comprising a 20 μL 1% HA disc. The reduced loading density of E2 had the predictable effect of lowering the release level of E2 after 3 days from 1.7 mg/L for the baseline gel to 1.6 mg/L. The next bar to the right represents the E2 release for an HA disc having a higher mass percent of HA, increased from 1% for the baseline gel to 2%, while still comprising a 20 μL HA disc loaded with 30% E2. The increased mass percent of HA had the effect of lowering the release level of E2 after 3 days from 1.7 mg/L for the baseline gel to 1.6 mg/L. The next bar to the right, or the second bar from the left, represents the E2 release for an HA disc of a smaller size and therefore higher surface area-to-volume ratio than the baseline gel, reducing the size from 20 μL to 10 μL. The reduced size of HA disc had the effect of lowering the lease level of E2 after 3 days from 1.7 mg/L for the baseline gel to 1.45 mg/L. This reduced release of E2 may have been due to a reduced amount of E2 loaded in the HA disc, since the smaller size HA disc would be predicted to have a higher release rate than the larger disc. This prediction was shown to be true for the initial release measured at 24 hours, where the amount of E2 released was greater from the 10 μL than from the 20 μL. Finally, the leftmost bar represents the E2 release for HA discs in the presence of hyaluronidase enzyme. Predictably, the exposure of HA discs to hyaluronidase enzyme results in an increased E2 release level from 1.7 mg/L for the baseline gel to the saturation level of the incubation medium of 2.25 mg/L. Thus, the presence of hyaluronidase enzyme may be able to even further increase the rate of E2 release in systems that saturate at higher concentration levels of E2.

Formulation of E2 into Microspheres

Figure 10:
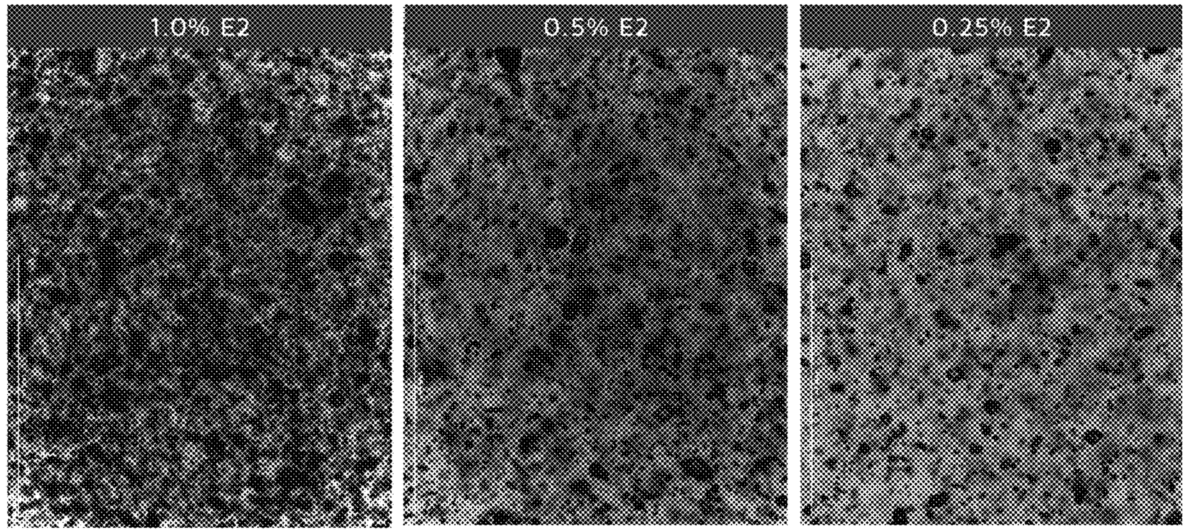
FIG. 10 illustrates the particles in solutions of 0.25% to 1.00% E2.

When working with the discs, there was an indication that the E2 powder would pose problems when run through the Likarda® CSS instrument due to E2 particle agglomeration from the powder. FIG. 10 illustrates the E2 hydrogel microparticles in solutions of 0.25%, 0.5%, and 1.00% E2. The particle diameters averaged between 12-14 μm which is at the limit of extrusion for some molecules especially when working at high loading densities such as the 30% E2 loading density tested in the disc format.

In fact, when the 20% E2 in a 2% HA formulation was run through the CSS instrument, some clogging of the extrusion nozzle resulted.

Figure 11:
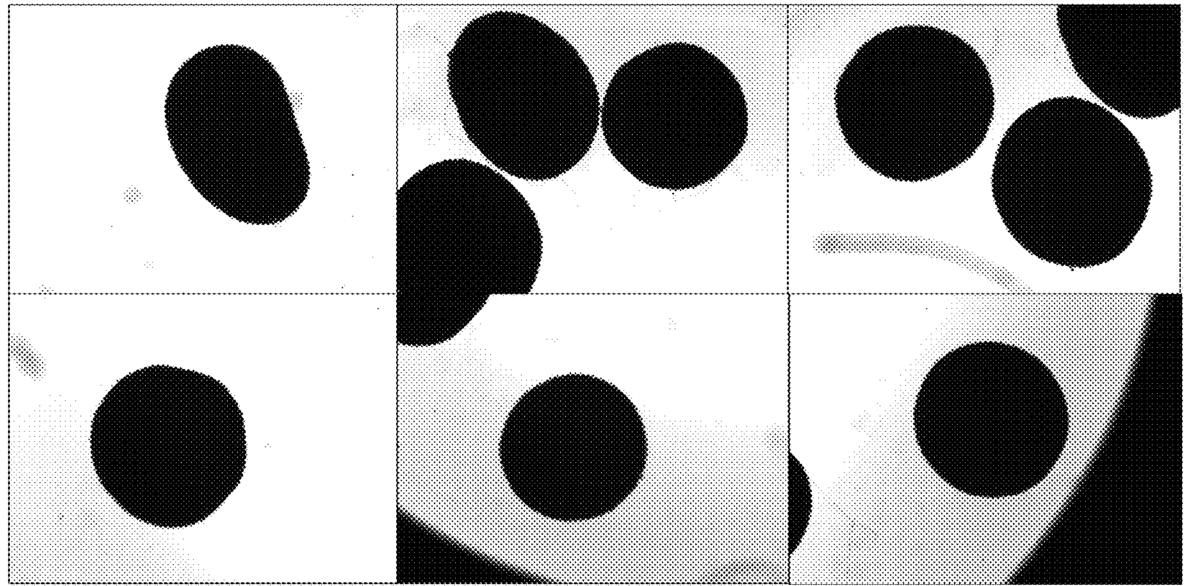
FIG. 11 shows images of the E2 microspheres formed at 20%.

FIG. 11 shows a highly magnified image of hydrogel microparticles, which illustrates the shape and uniformity of the microspheres produced, which were good. The microspheres produced had an approximately spherical shape and uniform size among the sample.

A supplier of higher quality micronized E2 was located. Upon receiving the higher quality micronized formulation of E2, some early observations were made. First, the micronized E2 is sticky and sticks to the tubing used in the Likarda CSS instrument. It also seems to foam when mixed with the HA.

Figure 12:
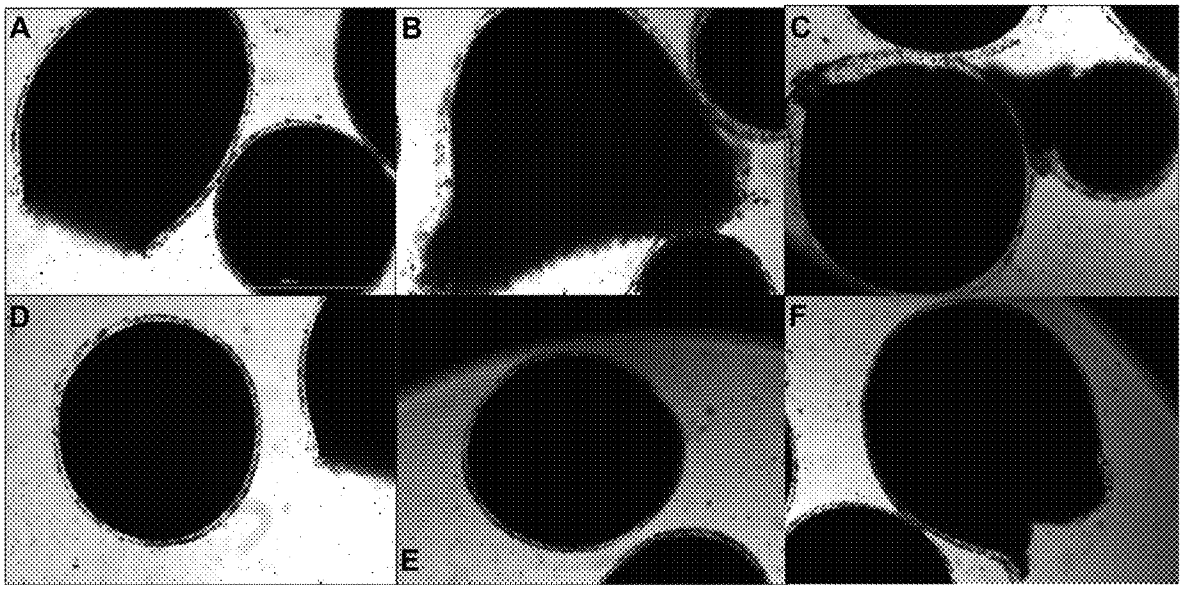
FIG. 12 shows images of the E2 microspheres formed from the micronized E2 at 25% E2 and 2.5% HA.

Microspheres loaded with 20% E2 were produced from the micronized E2 using Likarda's CSS instrument. In the initial run, there was less clogging of the nozzle than from powder E2, but the quality of the microspheres was poorer. FIG. 12 provides examples of the microspheres that resulted from the micronized E2 loaded into 2.5% HA particles. As can be seen in the images, the resulting droplets were not uniform in size (see images A and C), spherical in shape (see images A, B, C, and F), and the edges of the microparticles were not sharp/distinct/clean (see images A, B, D, and F). These microparticle characteristics indicate that the hydrogel precursor solution containing E2 material did not pass through the CSS instrument process smoothly, continuously, or correctly. In addition, there was still some clogging of the Likarda CSS instrument nozzles.

Figure 13:
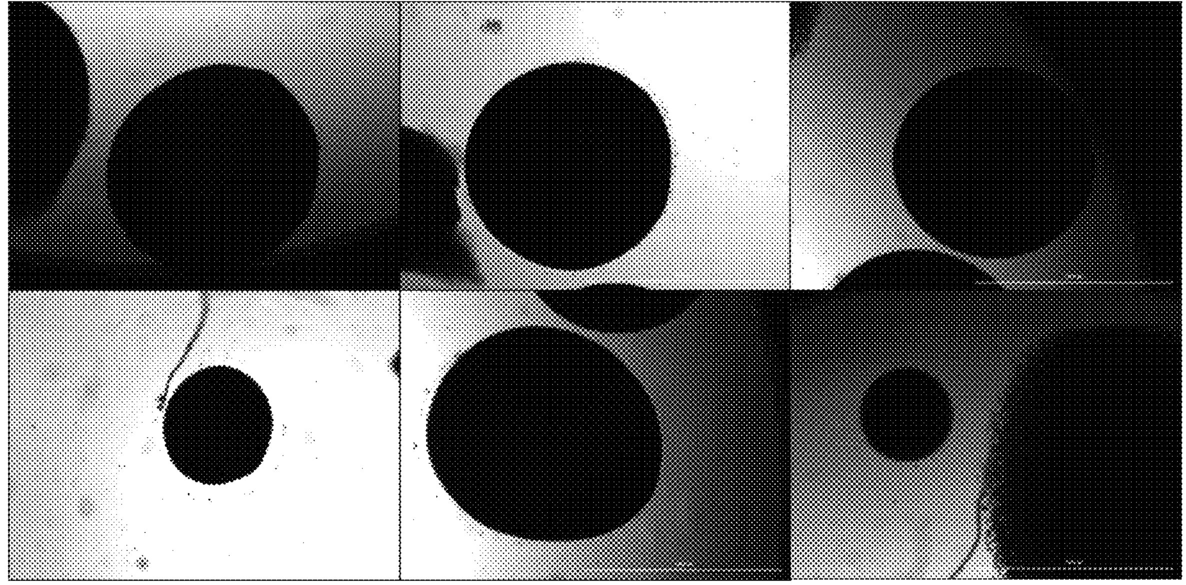
FIG. 13 shows images of the E2 microspheres formed from the micronized 15% E2 and 2% HA.

Five different iterations to the hydrogel precursor solution formulation were tested with the goal of smooth microspheres in the correct spherical shape. FIG. 13 illustrates the results from one batch of microspheres for one formulation producing uniformly size spherical microparticles. In order to achieve the improved results, the E2 concentration was reduced to 15% in a 2% HA solution. This resulted in the spherical shaped microspheres with smooth, sharp surfaces.

Figure 14A:
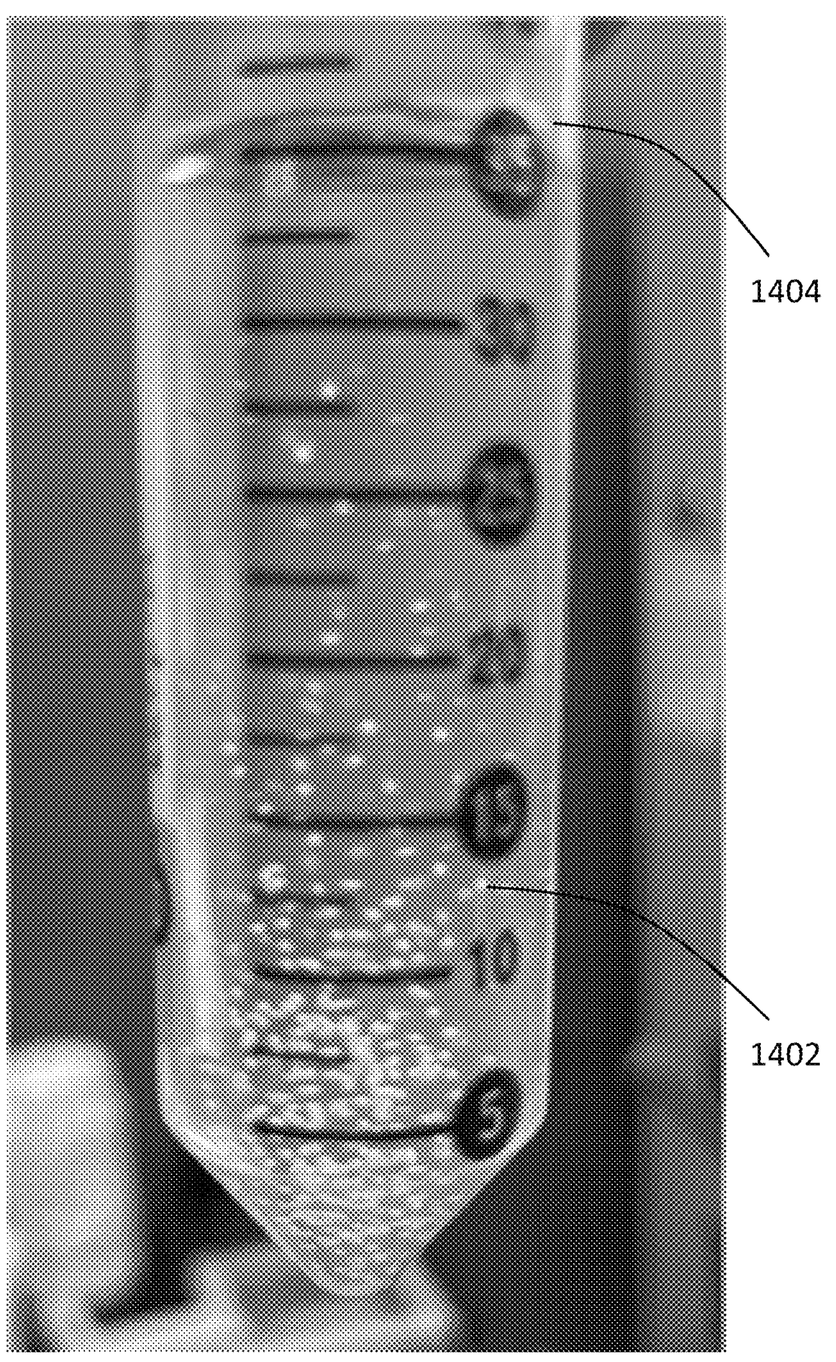
FIG. 14A shows E2-containing microspheres having consistent diameter and circularity in solution.
Figure 14B:
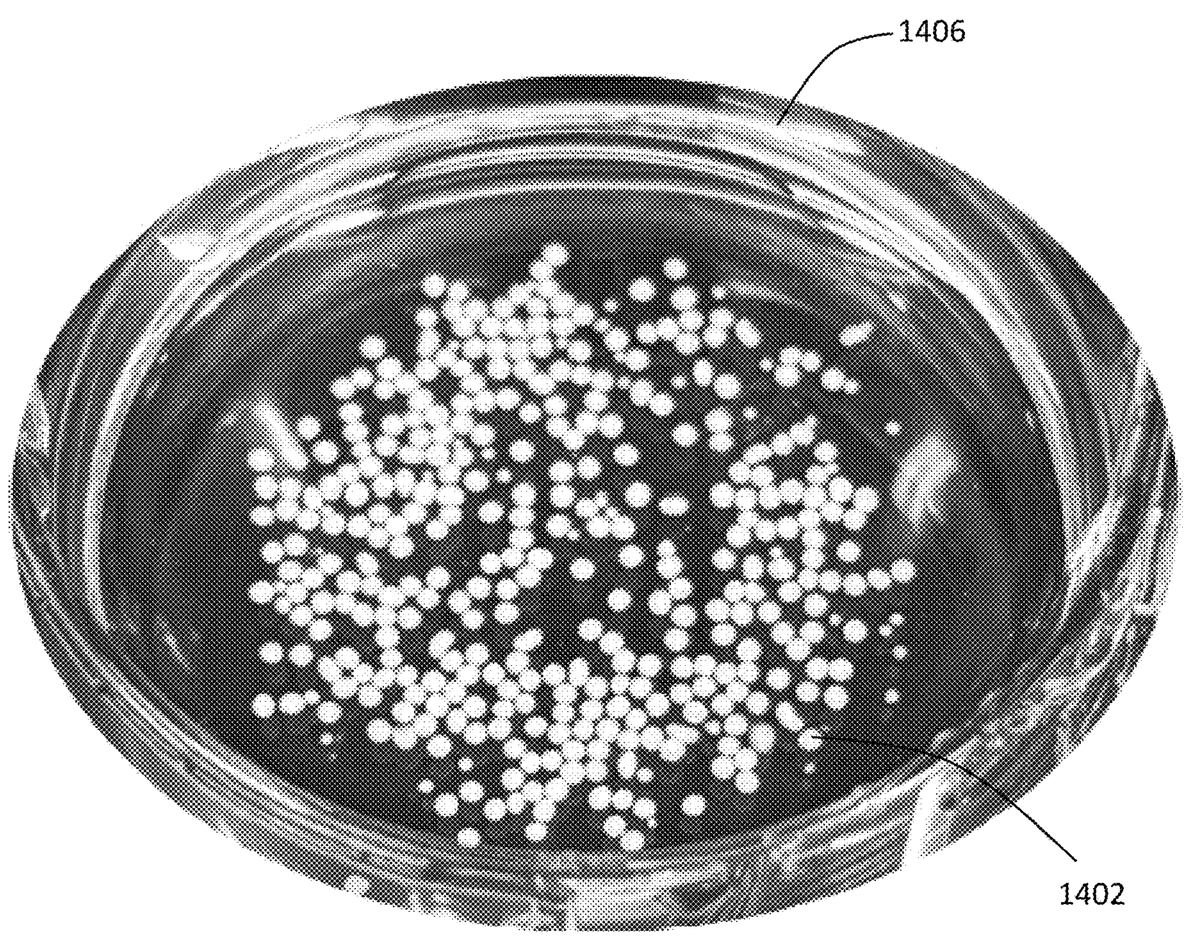
FIG. 14B shows E2-containing microspheres having consistent diameter and circularity in a dish.

The consistency of the microspheres formed from the 15% E2 in a 2% HA formulation is shown in FIGS. 14A and 14B. In FIG. 14A, the microspheres 1402 are shown in solution in a test tube 1404. In FIG. 14B, the microspheres 1402 are shown spread across the bottom of a microplate well 1406.

Figure 15:
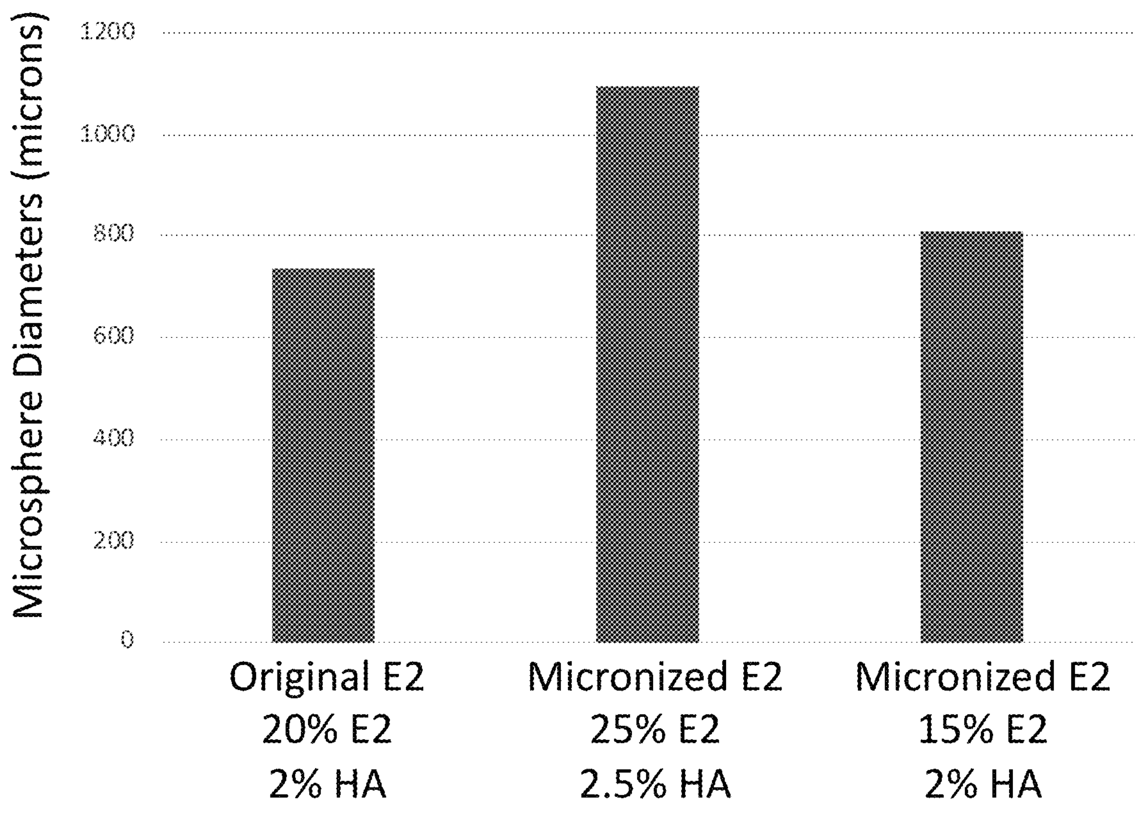
FIG. 15 shows the average diameter of the resulting microspheres for the different formulations.

With reference now to FIG. 15, there is shown a comparison of the average diameters of the microspheres resulting from three of the illustrative formulations. The original E2 formulation (20% E2 in 2% HA) had the smallest diameter when microspheres were formed, about 750 μm. Increasing both the E2 content and HA % to 25% micronized E2 in 2.5% HA resulted in the largest microsphere diameters, about 1100 μm. Lowering only the E2 concentration from the original formulation to 15% increased the size of the resulting microspheres as compared to the original formulation to about 800 μm, which can be preferable for an injectable product over the larger microspheres produced with both increased E2 and HA content.

Figure 16:
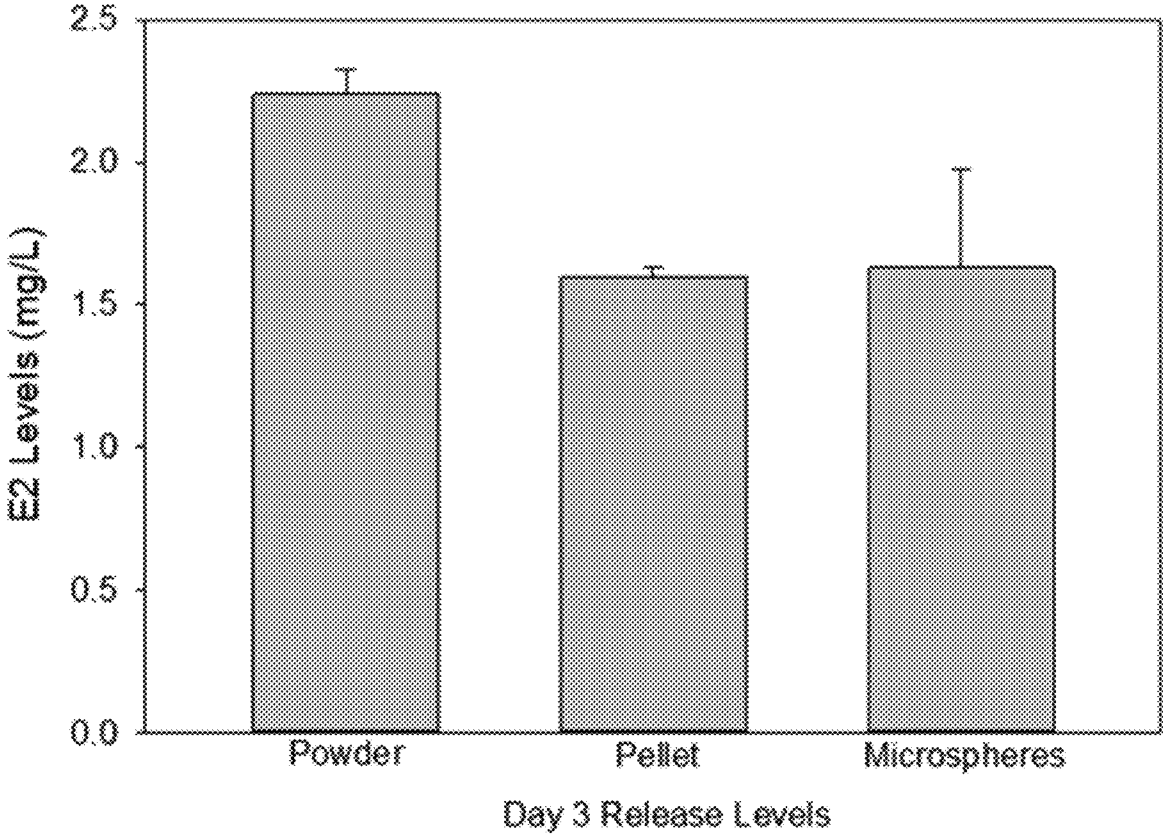
FIG. 16 shows average release levels for the E2 powder, pellet and microspheres.

The final microbead formulation resulted in a release profile that matched the pellet rate. FIG. 16 illustrates this conclusion by showing the E2 release levels on day 3 for the E2 powder, pelleted E2, and E2 containing microspheres. The powder mixed in the solution approximates the saturation level of E2 in the incubation medium. The release rate for the E2 pellet and microspheres are statistically indistinguishable. The only difference is noted in the variance around the mean showing that there is more variance between runs of the microspheres than for the pellets. This was due to a single run that resulted in a much higher release of E2, about 2.16 mg/L. If that run is removed from the data set, the average release level for the E2 microspheres falls to 1.36+/−0.07 mg/L, which is lower than the pellet level.

The non-micronized version of E2 behaved optimally in the hyaluronic acid hydrogel in bulk form but currently could not be utilized for making microspheres. The micronized version did make spheres, but initially they were of poor quality and the higher concentrations currently could not be utilized. Thus, the final formulation of micronized E2 at 15% in hyaluronic acid microspheres met both the release profile requirements and manufacturing standards. The E2 microspheres had a release profile that met the target of the E2 pellet that is currently used clinically as a hormone replacement.

Although the inventors hypothesize that E2 (estradiol) and testosterone will operate similarly during the MHA encapsulation process described herein, various tests were also performed with testosterone.

T Particulate Calculation

Figure 17A:
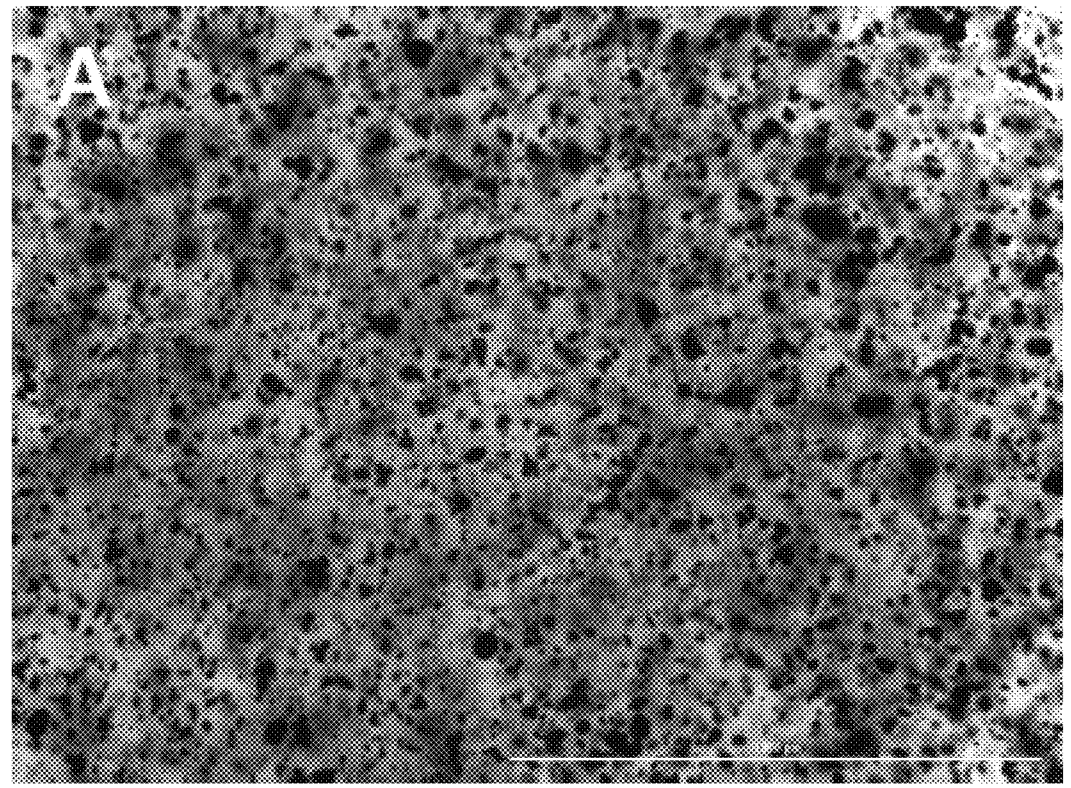
FIG. 17A shows an image of testosterone particles suspended in hydrogel at time 0.
Figure 17B:
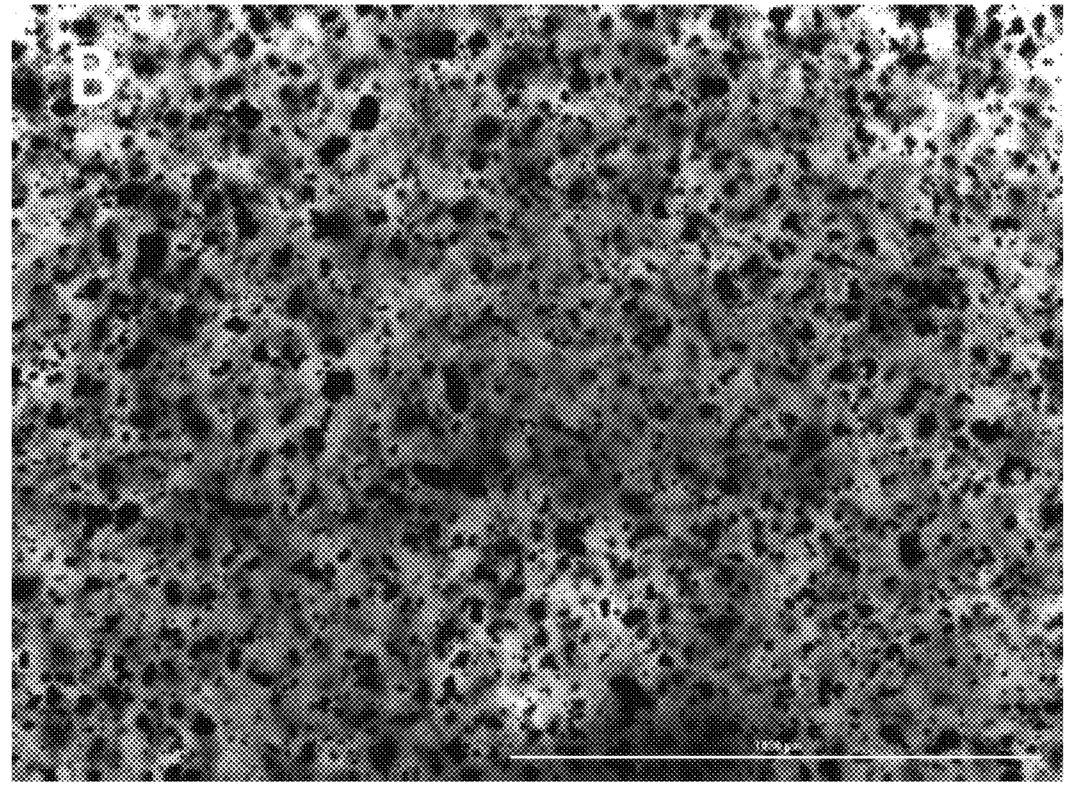
FIG. 17B shows an age of testosterone particles suspended in hydrogel at 72 hours.

One objective when preparing testosterone (T) encapsulated in hydrogel was to achieve an even distribution of encapsulated T particles with little or no aggregation and no immediate dissolution. Thus, initial studies focused on suspension of T in hydrogel. During the first several attempts, there was an initial issue of the T settling to the bottom of the hydrogel. The addition of a viscosifier or viscosity modifier to the hydrogel precursor solution reduced settling of the T particles and reduced oxygen inhibition of the hydrogel crosslinking. FIGS. 17A and 17B display the particulate density and size from one experimental study, though several were performed. Over the duration of several 3-day studies, the particulate size did not change significantly, indicating that the particles did not aggregate, which would have increased the measured size of the particulates. FIG. 17A is an image of T particles suspended in a hydrogel from one study at time 0, or within the first hour of generation of the hydrogel. FIG. 17B is an image of T particles suspended in the same hydrogel 72 hours later. Table 5 below summarizes the statistical analysis of the multiple experiments.

TABLE 5

| Parameter | 0 Hours | 72 Hours |
|---|---|---|
| Diameter (mm) | 13.98 +/− 0.37 | 12.675 +/− 0.36 |
| Area ($mm^2$) | 314.25 +/− 15.13 | 261.75 +/− 17.28 |

The measurements recorded in Table 5 show that there was no aggregation of particulates. Rather there was a reduction in diameter and area as would be expected with dissolution of the active ingredient (T).

Extrusion Parameter Optimization for Hydrogel Encapsulated T

A study was conducted to optimize hydrogel encapsulated T extrusion parameters by reducing clogging and sputtering of the extrusion tip and thereby yield relatively homogenous microspheres with the highest concentration of T possible.

Table 6 below provides the default or original parameters of the Likarda CSS extrusion process, as well as the modified extrusion parameters tested.

TABLE 6

| Parameter | Original Settings | Settings A | Settings B | Settings C | Settings D |
|---|---|---|---|---|---|
| Fluid speed (mL/min) | 1.0 | 1.0 | 1.4 | 1.5 | 1.25 |

TABLE 6-continued

| Parameter | Original Settings | Settings A | Settings B | Settings C | Settings D |
|---|---|---|---|---|---|
| Air flow rate (L/min) | 2 | 2 | 2.5 | 2.0 | 2.5 |
| UV exposure (mW/cm$^2$) | 20 (UV-A) | 20 (UV-A) 6 (UV-B) | 20 (UV-A) 6 (UV-B) | 20.1 (UV-A) 6 (UV-B) | 20.1 (UV-A) 6 (UV-B) |
| Precursor T (° C.) | RT* | RT | RT | 37 | 60 |

*RT = Room Temperature or about 25° C.

Figure 18:
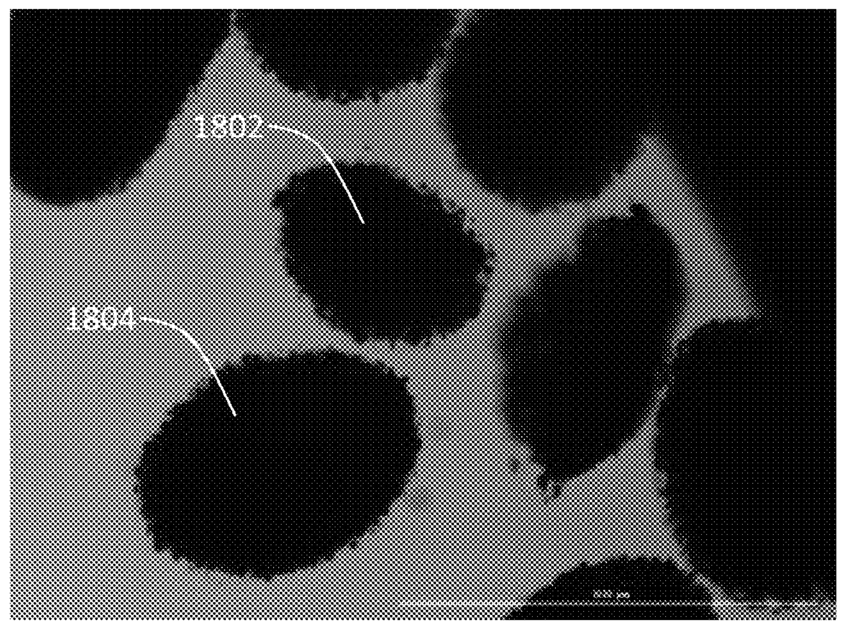
FIG. 18 shows hydrogel microspheres produced using the original settings for the Likarda CSS extrusion instrument.

The original settings outlined above in Table 6 resulted in excess sputtering of the hydrogel product during extrusion and relatively heterogenous diameter microspheres, as shown in FIG. 18. Microparticles 1802 and 1804 illustrate the faults of the microspheres produced with the original settings. Microparticle 1802 is about 40% smaller than microparticle 1804, while all microparticles lack sharp, distinct borders.

Settings A comprised a higher fluid pump rate and a higher air flow rate, as well as physical blockers to obstruct UV light exposure of the hydrogel precursor solution in the ejection syringe prior to extrusion. Settings A resulted in less sputtering, but one temporary clog during the microsphere manufacturing process. Additionally, the heterogeneity of the microsphere size was diminished with Settings A. However, "folds" appeared in the extrusion syringe indicating a chemical change in the hydrogel precursor solution before extrusion.

In Settings B, increasing both the fluid and air flow rates was tested, along with the UV blocker. Settings B resulted in increased extrusion nozzle clogging and more sputtering. However, the folds in the extrusion syringe decreased.

In Settings C, the fluid pump rate was further increased to 1.5 mL/min while the air flow rate was decreased back to the default value of 2 L/min. Additionally, the hydrogel precursor solution was heated to 37° C. prior to insertion into the CSS instrument. Settings C generally failed to generate microspheres, and instead generated streams of the hydrogel precursor solution. Even when Settings C did generate microspheres, they were extremely large, nearly twice the diameter of microspheres produced with the other instrument settings.

Due to the negative results from Settings C, in Settings D the fluid rate was decreased somewhat to 1.25 mL/min, the air flow rate was increased to 2.5 L/min, and the hydrogel precursor solution was further heated to 60° C. prior to insertion into the CSS instrument. Settings D parameters decreased clogging and sputtering to the minimum of any of the setting parameters and yielded more homogenous microspheres of the desired smaller size.

Figure 19:
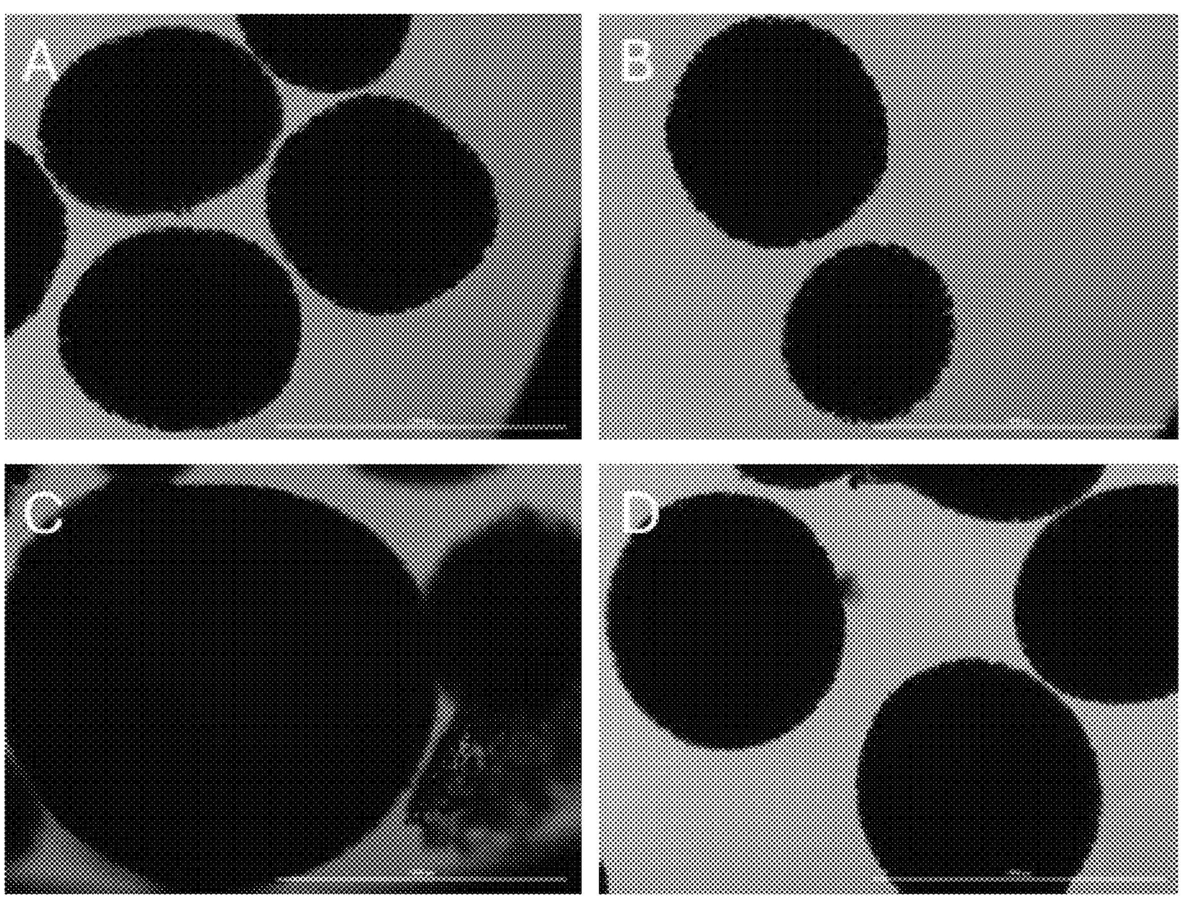
FIG. 19 shows exemplary images of microspheres generated from Settings A, Settings B, Settings C, and Settings D.

With reference now to FIG. 19, there are shown exemplary images of microspheres generated from Settings A, Settings B, Settings C, and Settings D in corresponding panes (A, B, C, and D) of FIG. 19. In pane A, the diminished heterogeneity of the microparticles is evident from the relatively uniform size of the imaged microparticles. In pane B, while the heterogeneity in size of the microparticles increases somewhat compared to those produced with Settings A, the produced microparticles still exhibit diminished heterogeneity compared to microparticles generated with the original instrument settings. In pane C, the greatly increased size of the microparticles produced is evident when compared to the scaled images of panes A, B, and D. In pane D, the most desirable and homogenous microparticles are present. Notably, all microspheres produced while optimizing the CSS instrument settings display loosely bound T particles on the surface of the microspheres.

Mechanical and Chemical Procedures to Clean Microsphere Surface

To remove T particles loosely bound to the exterior surface of hydrogel microspheres, different concentrations of ethanol along with mechanical stirring were tested. Table 7 summarizes the different mechanical and chemical approaches tested.

TABLE 7

| Mech. Approach | EtOH Conc. | Temp | Duration | Results |
|---|---|---|---|---|
| Stirred | 30% | 37° C. | 30 min | T leached out |
| Stirred | 20% | 37° C. | 30 min | Thin exterior film and clean surface |
| Stirred | 25% | 37° C. | 30 min | Optimal T conc. in supernatant and clean surface |

Figure 20A:
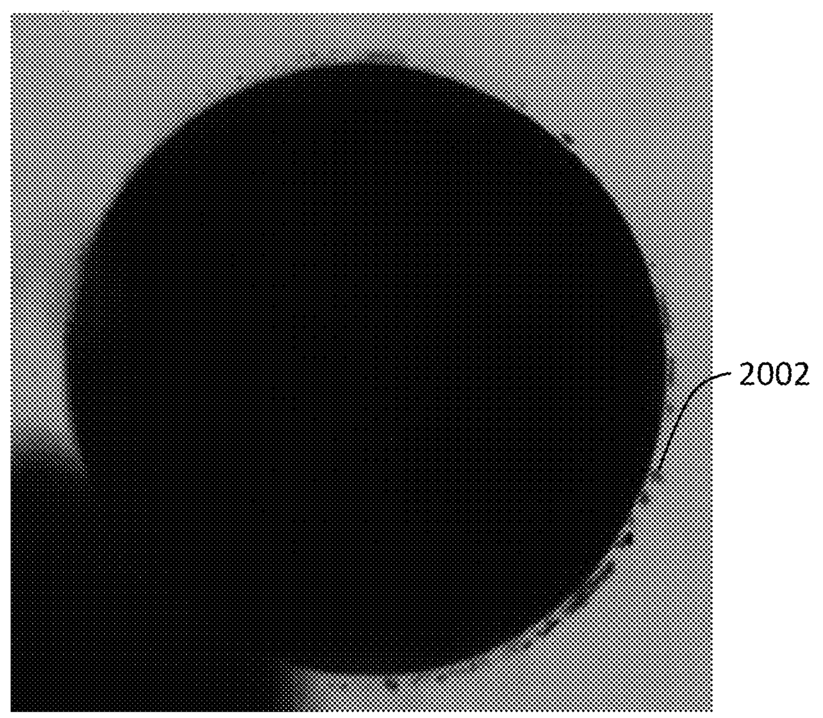
FIG. 20A shows testosterone particles on the surface of a hydrogel microsphere.
Figure 20B:
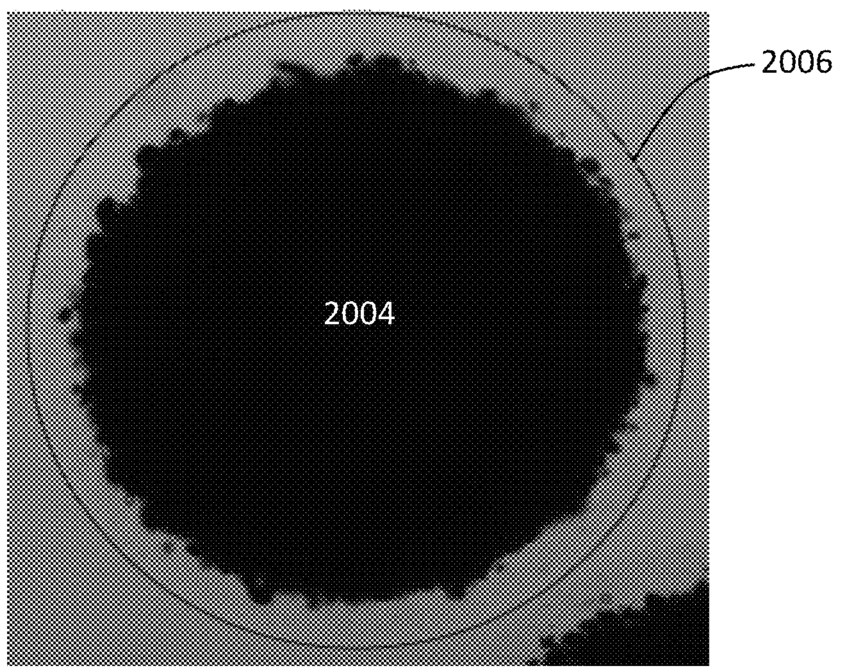
FIG. 20B shows a hydrogel microsphere from which testosterone has been leached out of a portion of the hydrogel microsphere near the exterior surface.

FIG. 20A depicts T particles 2002 on the surface of a microsphere. FIG. 20B shows T leaching from the portions of the microsphere near the exterior surface. The microparticle 2004 shown in FIG. 20B lacks any T (represented as black particles) in the outer layer of the microsphere as evidenced by the clear halo surrounding the microsphere core and within the outer border 2006 of the microparticle. From tests of these washing procedures and examination of the supernatant, inventors determined that stirring the microspheres in 25% concentration of ethanol at 37° C. for 30 minutes is the optimal washing procedure.

Maximum Allowable Loading Density of T

Testosterone (T) has a much higher solubility factor in water compared to E2, which raised the concern that T would diffuse out of the hydrogel at a rate too fast for the goal of the product. In light of this concern, it was determined that the maximum appropriate mass loading for T in the hydrogel was 30%.

T Release Rate Comparison

Figure 21:
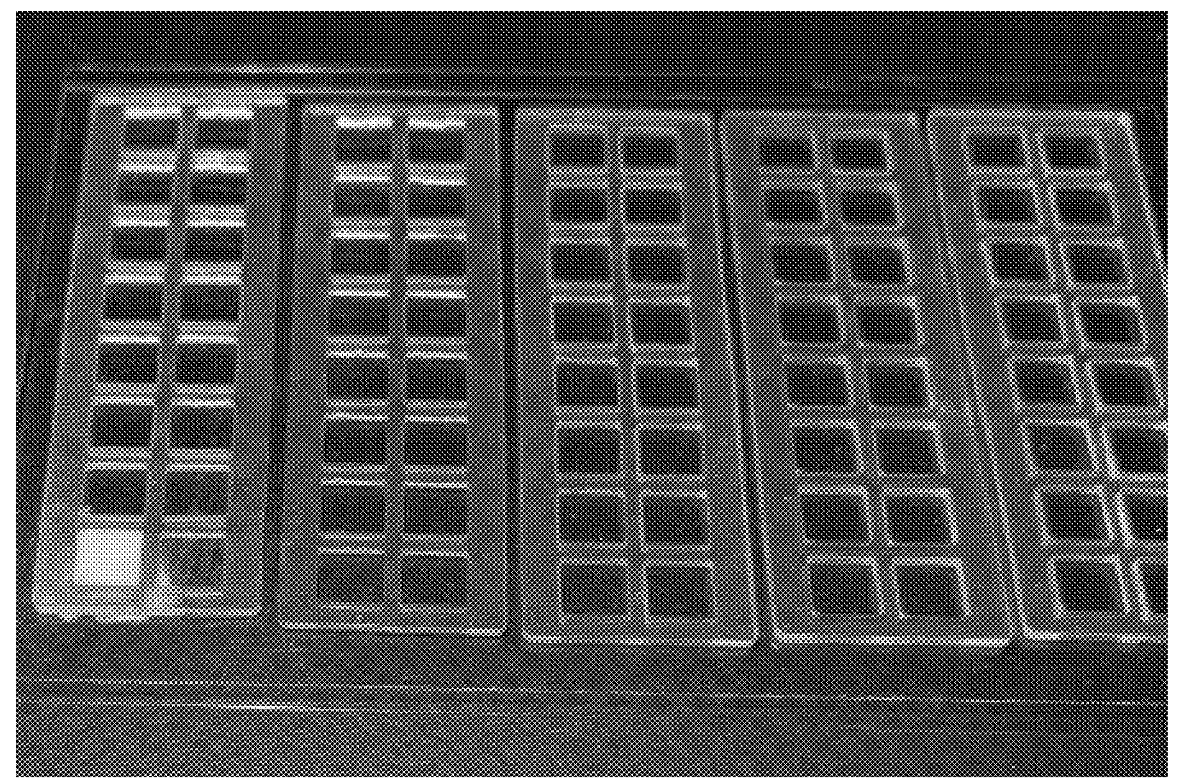
FIG. 21 shows Likarda's patented micromolds containing large 83 mg hydrogels containing testosterone.

In order to compare the release rate results of hydrogel encapsulated T to pelleted T, larger gels had to be prepared as the T pellets which the hydrogels are intended to replace are 25 mg, where the E2 pellets are merely 6 mg. Thus, approximately 83 mg of hydrogel at 30% T loading and 1% HA were prepared. In order to achieve even or consistent crosslinking in these much larger hydrogel samples, Likarda's patented micromolds (shown in FIG. 21) were employed. After formation, the encapsulated T was removed from the molds and placed in tubes to be rotated for an hour. The encapsulated T hydrogels were then removed from the tubes and stored in Dulbecco's PBS buffer. The large hydrogel blocks encapsulating T were then tested and compared to 25 mg T pellets and micronized T powder.

The T powder was produced as a 2.5 mg/mL slurry in buffer to reach the near saturation point of T in the buffer. Samples of the T powder slurry were removed from only the top layer of the slurry fluid to avoid aspirating T particles in the slurry that may have precipitated at to the bottom. T pellets were collected directly from the vials in which they were stored. The 83 mg hydrogels containing 30% T were collected from Dulbecco's PBS buffer, rinsed, and dried. Each of the collected samples was then placed in a separate container of incubation media (saline in this instance) for the release studies.

Samples of the respective incubation media for the T powder, pelleted T, and hydrogel encapsulated T were collected at 4, 24, and 48 hours, with 2-3 replicates from each experimental group at each collection time. All collected samples were then diluted before assaying for released T in the incubation media. Initially, the samples collected at 4 hours were diluted 400-fold, while the samples collected at 24 and 48 hours were diluted 1600-fold. These dilution values were based on the methods found appropriate for the E2 release experiments, but were insufficient for the T release studies as all samples collected for all three time points displayed T-saturation. As a result, dilution testing was performed at dilutions of 1200, 1600, 1800, 2200, 2400, and 3000-fold. From this dilution testing, 3000-fold dilution was found to be most appropriate for T release assays.

Figure 22:
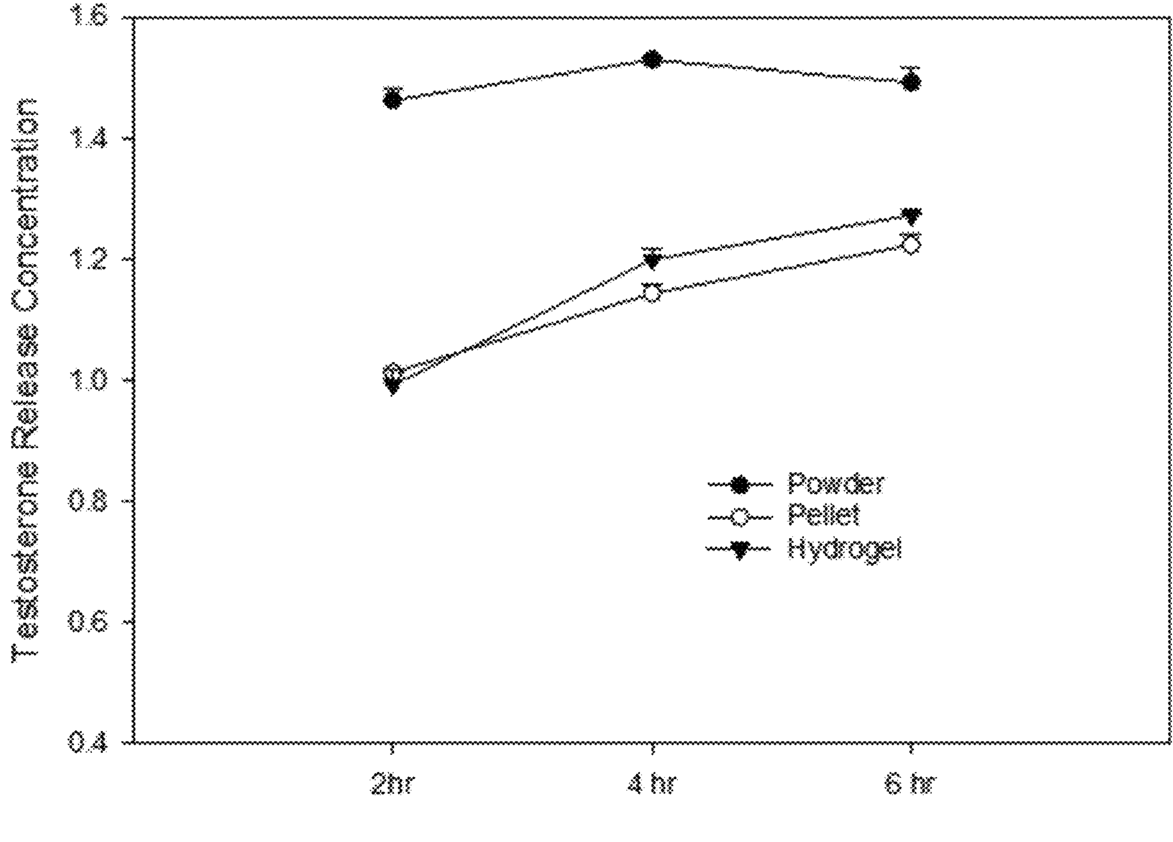
FIG. 22 shows the results of testosterone release studies of testosterone powder, pelleted testosterone, and hydrogel encapsulated testosterone at 2, 4, and 6 hours.

FIG. 22 shows the results of T release studies of T powder, T pellets, and hydrogel encapsulated T at 2, 4, and 6 hours. The T release levels for the T powder illustrate the approximate saturation level of T in saline of about 1.5 mg/L. As expected, based upon the previous E2 release studies, the T release levels from T pellets and hydrogel encapsulated T were very similar, to the point of being statistically insignificant throughout the study time range. However, at time points beyond 6 hours T release levels for all samples were saturated, yielding no useful data and requiring that the assay be halted. While this limited the determinations that could be made from the release study, the study was successful in determining the hydrogel encapsulated T formulation yielding a short-term T release profile matching that of pelleted T.

Treatment of Diseases

The hydrogels and microbeads described herein may be used for hormone therapies, such as menopause and low testosterone. During menopause, individuals experience symptoms including hot flashes, sleep disturbances, and night sweats. Sufferers of low testosterone experience chronic fatigue, loss of muscle mass, increased body fat (especially in the waist area), decreased bone mass, mood changes, lower mental capacity, depression, brain fog, and irritability. Testosterone helps regulate heart function, and plays a part in sperm production, bone health, energy levels, concentration, and muscle mass. Most men experience a natural decline in testosterone as they age, creating a large market for testosterone replacement therapy. In some instances, a disease or condition can include menopause, andropause, a cardiovascular condition, an erectile dysfunction, a diminished libido, a hot flash, a vaginal discomfort, a vaginal dryness, a sweating, a Parkinson's disease, an Alzheimer's disease, a metabolic syndrome, a diabetes, or any combination of these.

In some cases, an additional therapy can be administered to a subject to treat a disease or condition. In some embodiments, an additional therapy (e.g., a second therapy) can be administered to a subject in a unit dose. In some cases, 1, 2, 3, 4, 5 or more therapies can be administered to a subject in need thereof. In some cases, additional therapy can be administered consecutively or concurrently to a first therapy.

In some embodiments, a therapy can be administered to a subject in a unit dose. A unit dose that is administered to a patient may comprise from about 0.0001 g-500 g, 0.001 g-250 g, 0.01 g-100 g, 0.1 g-50 g, 10 g-25 g, 0.1 g-5 g, 0.1 g-1 g, or 1 g-10 g of a pharmaceutical composition of the current disclosure. In some embodiments, a pharmaceutical composition comprises an amount of at least about, or equal to about: 0.0001 g, 0.001 g, 0.01 g, 0.1 g, 0.5 g, 1 g, 2 g, 3 g, 4 g, 5 g, 6 g, 7 g, 8 g, 9 g, 10 g, 11 g, 12 g, 13 g, 14 g, 15 g, 16 g, 17 g, 18 g, 19 g, 20 g, 21 g, 22 g, 23 g, 24 g, 25 g, 26 g, 27 g, 28 g, 29 g, 30 g, 31 g, 32 g, 33 g, 34 g, 35 g, 36 g, 37 g, 38 g, 39 g, 40 g, 41 g, 42 g, 43 g, 44 g, 45 g, 46 g, 47 g, 48 g, 49 g, 50 g, 51 g, 52 g, 53 g, 54 g, 55 g, 56 g, 57 g, 58 g, 59 g, 60 g, 61 g, 62 g, 63 g, 64 g, 65 g, 66 g, 67 g, 68 g, 69 g, 70 g, 71 g, 72 g, 73 g, 74 g, 75 g, 76 g, 77 g, 78 g, 79 g, 80 g, 81 g, 82 g, 83 g, 84 g, 85 g, 86 g, 87 g, 88 g, 89 g, 90 g, 91 g, 92 g, 93 g, 94 g, 95 g, 96 g, 97 g, 98 g, 99 g, 100 g, 125 g, 150 g, 175 g, 200 g, 250 g, 300 g, 350 g, 400 g, 450 g, 500 g, or more of an active ingredient of the current disclosure. In some embodiments, a treatment herein can comprise from 0.001 g-2 g of an active ingredient of the current disclosure in a single dose. In some embodiments, an additional therapy comprises an amount between about 1 g-15 g of an active ingredient of the current disclosure of the current disclosure. In some embodiments, an additional therapy can be an amount from about 0.1 g-5 g of a therapeutic composition, a compound, or a salt thereof of the current disclosure.

Administration

A therapy or a composition disclosed herein can be administered by any method. In some embodiments, a composition or an additional therapeutic can be administered orally, for example, in the form of a liquid, a tablet, a pill, or a capsule. In some cases, a composition can be delivered by parenchymal injection, intra-thecal injection, intra-ventricular injection, intra-tumoral injection, intra-cisternal injection, or any combination thereof. In some cases, a method of administration can be by inhalation, intraarterial injection, intracerebroventricular injection, intracisternal injection, intramuscular injection, intraorbital injection, intraparenchymal injection, intraperitoneal injection, intraspinal injection, intrathecal injection, intravenous injection, intraventricular injection, stereotactic injection, subcutaneous injection, or any combination thereof. In some cases, delivery can comprise buccal administration, by infusion administration, nasal administration, otic administration, ophthalmic administration, sublingual administration, or transdermal administration. Delivery can include parenteral administration (including intravenous, subcutaneous, intrathecal, intraperitoneal, intramuscular, intravascular or infusion), oral administration, nasal administration, inhalation administration, anal administration, intraduodenal administration, rectal administration. In some cases, delivery can include delivery of a composition by a surgery, or by an injection. Delivery can include topical administration to an external surface, such as a skin. In some cases, a therapy disclosed herein can be administered consecutively or concurrently to an additional therapy.

In some instances, a composition or pharmaceutical composition may be in the form of a capsule, a tablet, a gummy, an oil, a syrup, a liquid, a tincture, a lotion, a cream, a balm, a food, a beverage, an oil, a suppository, a liquid for injection (which can be, for example, an intra venous liquid, an intra muscular liquid, a subcutaneous liquid), or any combination thereof.

In some embodiments, administering therapy and/or composition can be performed at least about: 1 time per day, 2 times per day, 3 times per day, 4 times per day, 5 times per day, 6 times per day, 7 times per day, or more than 7 times per day. In some cases, administering can be performed daily, weekly, monthly, or as needed. In some cases, administration can be performed at least 1, 2, 3, 4, 5, 6, 7, 8, 9, 10, 11, 12, 13, 14, 15, 16, 17, 18, 19, or 20 times a week. In some cases, administration can be performed at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, or 90 times a month.

Administration of a composition or a therapy disclosed herein can be performed for a treatment duration of at least about: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950 or 1000 days consecutive or nonconsecutive days. In some cases, a treatment duration can be from about: 1 to about 30 days, 1 to about 60 days, 1 to about 90 days, 30 days to about 90 days, 60 days to about 90 days, 30 days to about 180 days, from 90 days to about 180 days, or from 180 days to about 360 days.

In some aspects, the composition may be administered as needed. In some embodiments, administration of a composition or a therapy disclosed herein can be performed for a treatment duration of at least about 1 week, at least about 2 weeks, at least about 3 weeks, at least about 4 weeks, at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 1 year, at least about 2 years, at least about 3 years, at least about 4 years, at least about 5 years, at least about 6 years, at least about 7 years, at least about 8 years, at least about 9 years, at least about 10 years, at least about 15 years, at least about 20 years, or for life. In some cases, administration can be performed repeatedly over a lifetime of a subject, such as once a month, once a week, or once a year for the lifetime of a subject. Administration can be performed repeatedly over a substantial portion of a subject's life, such as once a month, once a week, or once a year for at least about 1 year, 5 years, 10 years, 15 years, 20 years, 25 years, 30 years, or more.

In one embodiment, a pharmaceutical composition of hydrogel microspheres containing a hormone may be administered to a patient by subcutaneous injection using a dual chamber syringe, such as that depicted in FIGS. 23 and 24. The dual chamber syringe 2300 depicted in FIGS. 23A-D is a bypass-type, while the dual chamber syringe 2400 depicted in FIGS. 24A-D is a separator piercing-type.

Figure 23A:
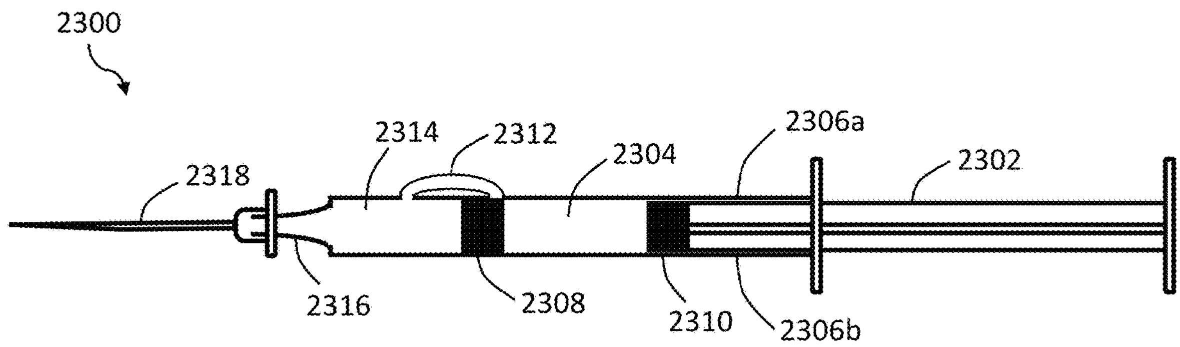
FIGS. 23A-D show an illustrative bypass-type dual chamber syringe for administration of hydrogel microbead therapies.

Referring now to FIG. 23A, there is shown the bypass-type dual chamber syringe 2300 in a fully extended position. In this fully extended position, the plunger 2302 is retracted so that the volume of a first chamber 2304 is maximized. The first chamber 2304 is defined by the sidewalls 2306*a* and 2306*b* of the syringe 2300, the end 2310 of the plunger 2302, and the separator 2308. Also in this fully extended position, the separator 2308 is located in a position blocking or closing one end of a bypass pathway 2312, while the other end of the bypass pathway opens into a second chamber 2314. The second chamber 2314 is defined by the sidewalls 2306*a* and 2306*b* of the syringe 2300, the separator 2308, and the anterior end of the syringe 2316. In some embodiments, the anterior end of the second chamber 2314 is defined by the needle 2318 instead of the anterior end of the syringe 2316.

Figure 23B:
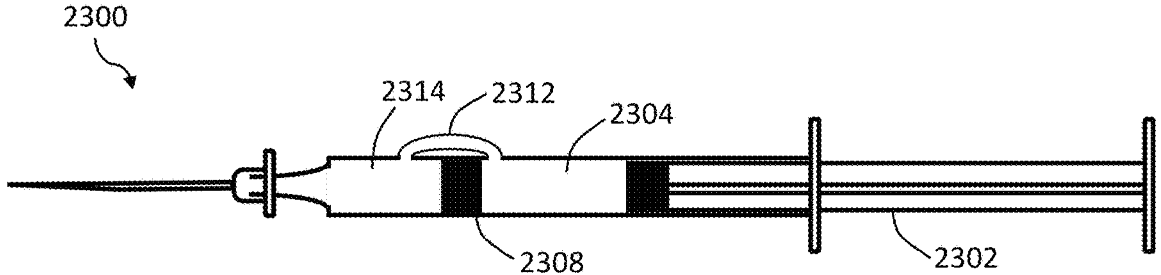

With reference now to FIG. 23B, there is shown the bypass-type dual chamber syringe 2300 in a position initially depressed from the fully extended position. In this position, the plunger 2302 has compressed a fluid in the first chamber 2304 and caused the separator 2308 to move to a position that does not obstruct the opening of the bypass 2312, thereby opening the bypass pathway 2312 from the first chamber 2304 to the second chamber 2314. When the bypass pathway 2312 is open, the contents of the first chamber 2304 and the contents of the second chamber 2314 may contact one another, intermingle, and/or mix.

Figure 23C:
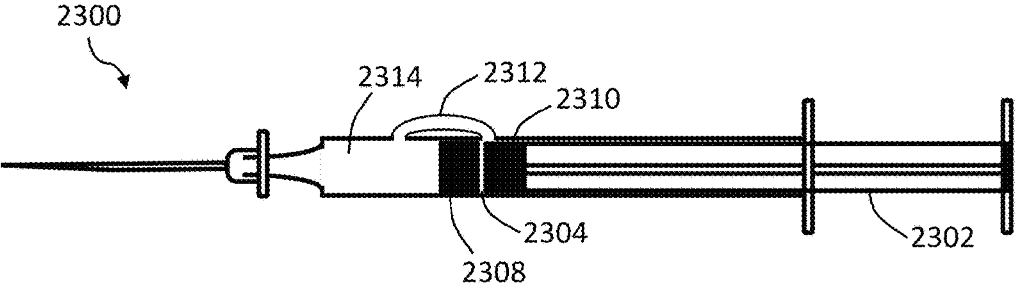

Referring now to FIG. 23C, there is shown the bypass-type dual chamber syringe 2300 in a position fully compressing the first chamber 2304. In this position, the plunger 2302 has been compressed to the point that the end 2310 of the plunger 2302 contacts or abuts the separator 2308, thereby decreasing the volume of the first chamber to a minimum size. Also in this position, compressing the plunger 2302 forces the contents of the first chamber 2304 through the bypass pathway 2312 into the second chamber 2314. When the plunger 2302 forces the contents of the first chamber 2304 through the bypass pathway 2312 into the second chamber 2314, the contents of the first chamber and the contents of the second chamber intermingle and/or mix. For a non-limiting example, where the first chamber contains a hydrogel solvent and the second chamber contains hydrogel microbeads encapsulating a hormone therapeutic agent, compressing the plunger 2302 causes the solvent to suspend and/or dissolve the hydrogel microbeads. In other examples, the first chamber may contain hydrogel microbeads encapsulating a hormone therapeutic agent and the second chamber may contain the hydrogel solvent.

Figure 23D:
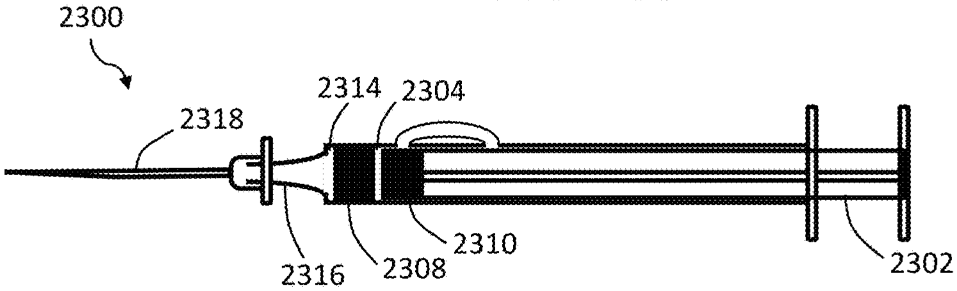

With reference now to FIG. 23D, there is shown the bypass-type dual chamber syringe 2300 in a position fully compressing the plunger 2302, first chamber 2304, and second chamber 2314. Once the end 2310 of the plunger 2302 contacts the separator 2308 (such as the position depicted in FIG. 23C), further depression or compression of the plunger 2302 causes the separator 2308 to move towards the anterior end 2316 of the syringe 2300 and compress the second chamber 2314. By compressing the second chamber 2314, the plunger 2302 forces a mixture of the contents of the first chamber and the contents of the second chamber out of the syringe 2300 through the needle 2318.

Figure 24A:
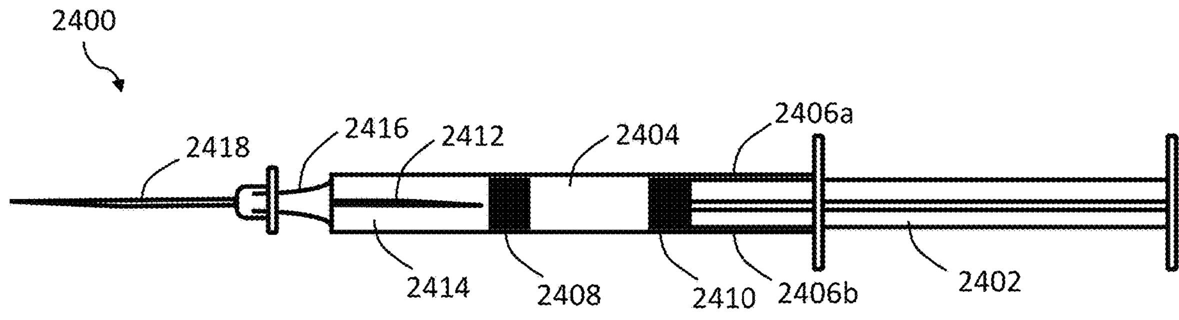
FIGS. 24A-D show an illustrative separator piercing-type dual chamber syringe for administration of hydrogel microbead therapies.

Referring now to FIG. 24A, there is shown separator piercing-type dual chamber syringe 2400 in a fully extended position. In this fully extended position, the plunger 2402 is retracted so that the volume of a first chamber 2404 is maximized. The first chamber 2404 is defined by the side-walls 2406*a* and 2406*b* of the syringe 2400, the end 2410 of the plunger 2402, and the separator 2408. Also in this fully extended position, the separator 2408 is located in a position out of contact from an internal needle 2412 and also between, and separating, the first chamber 2404 and a second chamber 2414. The second chamber 2414 is defined by the sidewalls 2406*a* and 2406*b* of the syringe 2400, the separator 2408, and the anterior end of the syringe 2416. In some embodiments, the anterior end of the second chamber 2414 is defined by the needle 2418 instead of the anterior end of the syringe 2416.

Figure 24B:
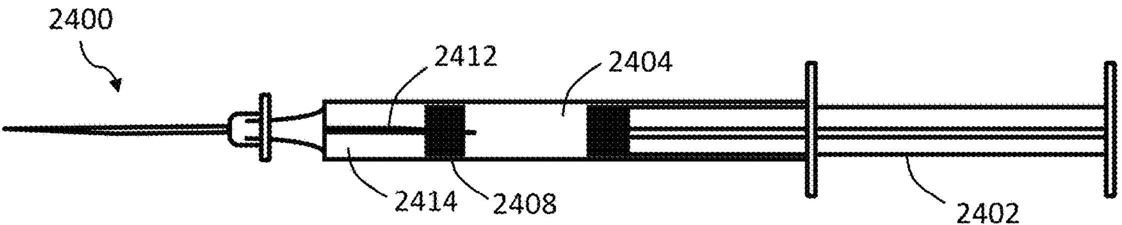

With reference now to FIG. 24B, there is shown the piercing-type dual chamber syringe 2400 in a position initially depressed from the fully extended position. In this position, the plunger 2402 has compressed a fluid in the first chamber 2404 and caused the separator 2408 to move to a position where the internal needle 2412 has pierced entirely through the separator 2408. The process of compressing or depressing the plunger 2402 from the fully extended position shown in FIG. 24A to the initially depressed position shown in FIG. 24B causes the separator 2408 to impact the tip of the internal needle 2412 and the internal needle 2412 to pierce the separator 2408. In the position shown in FIG. 24B, the internal needle 2412 has pierced entirely through the separator 2408 and provides a pathway for contents of the first chamber 2404 to flow or be forced into the second chamber 2414 where these contents may contact one another, intermingle, and/or mix.

Figure 24C:
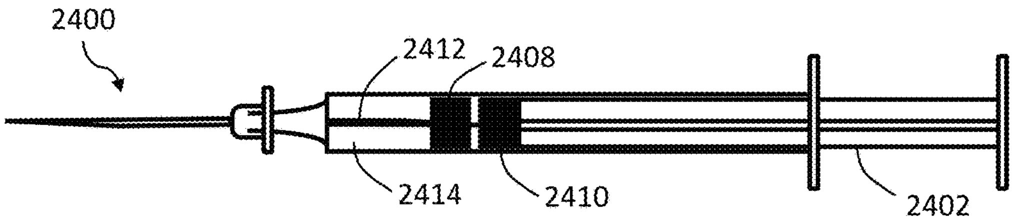

Referring now to FIG. 24C, there is shown the piercing-type dual chamber syringe 2400 in a position fully compressing the first chamber 2404. In this position, the plunger 2402 has been compressed to the point that the end 2410 of the plunger 2402 contacts or abuts the tip of the internal needle 2412 and/or the separator 2408, thereby decreasing the volume of the first chamber to a minimum size. Also in this position, compressing the plunger 2402 forces the contents of the first chamber 2404 through the internal needle pathway 2412 into the second chamber 2414. When the plunger 2402 forces the contents of the first chamber 2404 through the internal needle pathway 2412 into the second chamber 2414, the contents of the first chamber 2404 and the contents of the second chamber 2414 intermingle and/or mix. For a non-limiting example, where the first chamber 2404 contains a hydrogel solvent and the second chamber 2414 contains hydrogel microbeads encapsulating a hormone therapeutic agent, compressing the plunger 2402 causes the solvent to suspend and/or dissolve the hydrogel microbeads. In other examples, the first chamber 2404 may contain hydrogel microbeads encapsulating a hormone therapeutic agent and the second chamber 2414 may contain the hydrogel solvent.

Figure 24D:
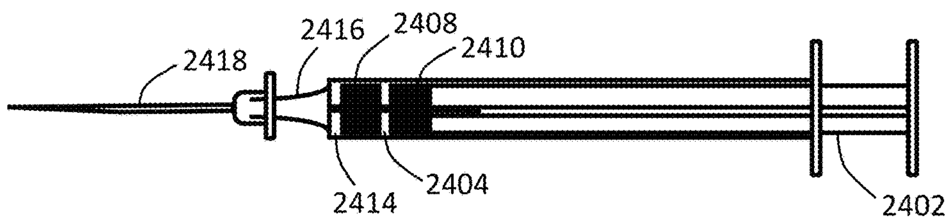

With reference now to FIG. 24D, there is shown the piercing-type dual chamber syringe 2400 in a position fully compressing the plunger 2402, first chamber 2404, and second chamber 2414. Once the end 2410 of the plunger 2402 contacts the separator 2408 (such as the position depicted in FIG. 24C), further depression or compression of the plunger 2402 causes the separator 2408 to move towards the anterior end 2416 of the syringe 2400 and compress the second chamber 2414. By compressing the second chamber 2414, the plunger 2402 forces a mixture of the contents of the first chamber and the contents of the second chamber out of the syringe 2400 through the needle 2418.

In some embodiments, the hydrogel microsphere formulations described herein may be provided as an element in a kit. An illustrative kit may include an outer package housing a hypodermic syringe, scalpel, scissors, bandages, antiseptic ointments, and a hydrogel container. The hydrogel container may be a sealed bottle or vile. The hydrogel container may be enclosed by a cap or plug that seals the container and allows a syringe needle to puncture cap/plug and penetrate to the interior of the container. Any one of the hydrogel formulations described herein may be enclosed within the hydrogel container.

It is to be understood that the detailed description of illustrative embodiments are provided for illustrative purposes. The scope of the claims is not limited to these specific embodiments or examples. Therefore, various process limitations, elements, details, and uses can differ from those just described, or be expanded on or implemented using technologies not yet commercially viable, and yet still be within the inventive concepts of the present disclosure. The scope of the invention is determined by the following claims and their legal equivalents.

What is claimed is:

1. A dual chamber syringe for administering a steroid hormone encapsulated by a hydrogel polymer, the dual chamber syringe comprising:

a first chamber that includes a crosslinked methacrylate hyaluronic acid (MHA) polymer that encapsulates the steroid hormone in the form of a plurality of hydrogel microparticles, wherein the crosslinked MHA polymer is the hydrogel polymer;

wherein the steroid hormone is selected from the group consisting of testosterone, estradiol, and the combination thereof;

wherein the crosslinked MHA polymer is generated by applying an ultraviolet light to an uncrosslinked MHA mixture that includes the steroid hormone, methacrylate hyaluronic acid, and sodium hyaluronate;

wherein the plurality of hydrogel microparticles are formulated for subcutaneous administration and to provide controlled release of the steroid hormone over a period of at least one (1) week;

a second chamber having a diluent for the crosslinked MHA polymer;

a separator that separates the first chamber from the second chamber, wherein piercing the separator generates a mixture that includes the diluent and the crosslinked MHA polymer that encapsulates the steroid hormone; and a plunger that forces the mixture through a needle.

2. The dual chamber syringe of claim 1 wherein the plunger pierces the separator, forces the crosslinked MHA polymer that encapsulates the steroid hormone from the first chamber through the separator to the second chamber, and causes the diluent and the crosslinked MHA polymer that encapsulates the steroid hormone to mix.

3. The dual chamber syringe of claim 1 wherein the plunger pierces the separator, causes the diluent from the second chamber through the separator to the first chamber, and causes the diluent and the crosslinked MHA polymer that encapsulates the steroid hormone to mix.

4. The dual chamber syringe of claim 1 wherein the steroid hormone includes a micronized testosterone.

5. A dual chamber syringe for administering a steroid hormone encapsulated by a hydrogel polymer, the dual chamber syringe comprising:

a first chamber that includes a crosslinked methacrylate hyaluronic acid (MHA) polymer that encapsulates the steroid hormone in the form of a plurality of hydrogel microparticles, wherein the crosslinked MHA polymer is the hydrogel polymer;

wherein the steroid hormone is selected from the group consisting of testosterone, estradiol, and the combination thereof;

wherein the crosslinked MHA polymer is generated by applying an ultraviolet light to an uncrosslinked MHA mixture that includes the steroid hormone, methacrylate hyaluronic acid, and sodium hyaluronate;

wherein the plurality of hydrogel microparticles are formulated for subcutaneous administration and to provide controlled release of the steroid hormone over a period of at least one (1) week;

a second chamber having a diluent for the crosslinked MHA polymer;

a separator that separates the first chamber from the second chamber when the separator is in a first position;

a bypass that connects the first chamber to the second chamber when the separator is in a second position;

wherein moving the separator from the first position to the second position generates a mixture that includes the diluent and the crosslinked MHA polymer that encapsulates the steroid hormone; and a plunger that forces the mixture through a needle.

6. The dual chamber syringe of claim 5 wherein the plunger moves the separator from the first position to the second position.

7. The dual chamber syringe of claim 6 wherein the plunger forces the MHA polymer that encapsulates the steroid hormone from the first chamber through the bypass to the second chamber when the separator is in the second position and causes the diluent and the crosslinked MHA polymer that encapsulates the steroid hormone to mix.

8. The dual chamber syringe of claim 6 wherein the plunger forces the diluent from the second chamber through the bypass to the first chamber when the separator is in the second position and causes the diluent and the crosslinked MHA polymer that encapsulates the steroid hormone to mix.

9. The dual chamber syringe of claim 5 wherein the steroid hormone includes a micronized testosterone.

10. The dual chamber syringe of claim 1 wherein the plurality of hydrogel microparticles are each formed by forming a core-shell microparticle comprising an outer alginate shell and a liquid core, crosslinking the liquid core with ultraviolet light, and removing the outer alginate shell with a chelating agent.

11. The dual chamber syringe of claim 10 wherein the chelating agent is selected from the group consisting of citrate, ethylenediaminetetraacetic acid, egtazic acid, phosphates, and mixtures thereof.

12. The dual chamber syringe of claim 1 wherein the plurality of hydrogel microparticles have an average diameter ranging from about 100 μm to about 1400 μm.

13. The dual chamber syringe of claim 1 wherein the controlled release of the steroid hormone extends over a period from one week to one month.

14. The dual chamber syringe of claim 1 wherein the dual chamber syringe is for treatment of hypogonadism.

15. The dual chamber syringe of claim 5 wherein the plurality of hydrogel microparticles are each formed by forming a core-shell microparticle comprising an outer alginate shell and a liquid core, crosslinking the liquid core with ultraviolet light, and removing the outer alginate shell with a chelating agent.

16. The dual chamber syringe of claim 15 wherein the chelating agent is selected from the group consisting of citrate, ethylenediaminetetraacetic acid, egtazic acid, phosphates, and mixtures thereof.

17. The dual chamber syringe of claim 5 wherein the plurality of hydrogel microparticles have an average diameter ranging from about 100 μm to about 1400 μm.

18. The dual chamber syringe of claim 5 wherein the controlled release of the steroid hormone extends over a period from one week to one month.

19. The dual chamber syringe of claim 5 wherein the dual chamber syringe is for treatment of hypogonadism.

* * * * *